United States Patent
Colson et al.

(10) Patent No.: US 10,844,057 B2
(45) Date of Patent: Nov. 24, 2020

(54) PROCESS FOR PREPARING JAK INHIBITORS AND INTERMEDIATES THEREOF

(71) Applicant: THERAVANCE BIOPHARMA R&D IP, LLC, South San Francisco, CA (US)

(72) Inventors: Pierre-Jean Colson, South San Francisco, CA (US); Gene Timothy Fass, South San Francisco, CA (US)

(73) Assignee: Theravance Biopharma R&D IP, LLC, South San Francisco, CA (US)

( * ) Notice: Subject to any disclaimer, the term of this patent is extended or adjusted under 35 U.S.C. 154(b) by 0 days.

(21) Appl. No.: 16/559,091

(22) Filed: Sep. 3, 2019

(65) Prior Publication Data

US 2020/0071324 A1    Mar. 5, 2020

Related U.S. Application Data

(60) Provisional application No. 62/726,600, filed on Sep. 4, 2018.

(51) Int. Cl.
*C07D 471/04* (2006.01)
*C07D 519/00* (2006.01)

(52) U.S. Cl.
CPC ......... *C07D 471/04* (2013.01); *C07D 519/00* (2013.01)

(58) Field of Classification Search
CPC ... C07D 471/04; C07D 519/00; C07D 401/04
USPC ....................................................... 546/118
See application file for complete search history.

(56) References Cited

U.S. PATENT DOCUMENTS

| | | | |
|---|---|---|---|
| 6,534,524 | B1 | 3/2003 | Kania et al. |
| 6,884,890 | B2 | 4/2005 | Kania et al. |
| 7,884,109 | B2 | 2/2011 | Ohlmeyer et al. |
| 8,450,340 | B2 | 5/2013 | Hood et al. |
| 8,575,336 | B2 | 11/2013 | Coe et al. |
| 8,648,069 | B2 | 2/2014 | Akritopoulou-Zanze |
| 8,895,544 | B2 | 11/2014 | Coe et al. |
| 10,100,049 | B2 | 10/2018 | Fatheree et al. |
| 10,183,942 | B2 | 1/2019 | Fatheree et al. |
| 10,196,393 | B2 | 2/2019 | Fatheree et al. |
| 10,208,040 | B2 | 2/2019 | Fatheree et al. |
| 10,251,874 | B2 | 4/2019 | Dabros et al. |
| 10,392,386 | B2 | 8/2019 | Fatheree et al. |
| 10,406,148 | B2 | 9/2019 | Thalladi et al. |
| 10,493,077 | B2 | 12/2019 | Fatheree et al. |
| 10,519,153 | B2 | 12/2019 | Fatheree et al. |
| 10,526,330 | B2 | 1/2020 | Fatheree et al. |
| 10,548,886 | B2 | 2/2020 | Thalladi et al. |
| 10,550,118 | B2 | 2/2020 | Fatheree et al. |
| 2005/0090529 | A1 | 4/2005 | McAlpine et al. |
| 2015/0158864 | A1 | 6/2015 | Thorarensen et al. |
| 2015/0329542 | A1 | 11/2015 | Coe et al. |
| 2016/0289196 | A1 | 10/2016 | Choi et al. |
| 2017/0121327 | A1 | 5/2017 | Fatheree et al. |
| 2018/0258088 | A1 | 9/2018 | Fatheree et al. |
| 2018/0311223 | A1 | 11/2018 | Dabros et al. |
| 2018/0311226 | A1 | 11/2018 | Thalladi et al. |
| 2018/0311255 | A1 | 11/2018 | Fatheree et al. |
| 2019/0119275 | A1 | 4/2019 | Fatheree et al. |
| 2019/0127371 | A1 | 5/2019 | Fatheree et al. |
| 2020/0046719 | A1 | 2/2020 | Fatheree et al. |
| 2020/0071323 | A1 | 3/2020 | Long et al. |
| 2020/0071325 | A1 | 3/2020 | Long et al. |
| 2020/0087303 | A1 | 3/2020 | Fatheree et al. |
| 2020/0121669 | A1 | 4/2020 | Thalladi et al. |
| 2020/0131178 | A1 | 4/2020 | Fatheree et al. |
| 2020/0181141 | A1 | 6/2020 | Fatheree et al. |

FOREIGN PATENT DOCUMENTS

| | | |
|---|---|---|
| JP | 2010111624 A | 5/2010 |
| WO | WO 2005/009389 A2 | 2/2005 |
| WO | WO 2010/114971 A1 | 10/2010 |
| WO | WO 2013/014567 A1 | 1/2013 |
| WO | WO 2015/173683 A1 | 11/2015 |
| WO | WO 2016/026078 A1 | 2/2016 |
| WO | WO 2017/077283 A1 | 5/2017 |
| WO | WO 2017/077288 A1 | 5/2017 |
| WO | 2020/173400 A1 | 9/2020 |

OTHER PUBLICATIONS

U.S. Appl. No. 62/751,967, Fatheree et al., Unpublished.
U.S. Appl. No. 16/511,410, Fatheree et al., Unpublished.
Abcouwer, "Angiogenic factors and cytokines in diabetic retinopathy", J Clin Cell Immunol, Supplement 1: 1-12 (2013).
Bao et al., "The involvement of the JAK-STAT signaling pathway in chronic inflammatory skin disease atopic dermatitis", JAK-STAT, 2(3): e24137-1-e24137-8 (2013). (1997).
Berastegui et al., "BALF cytokines in different phenotypes of chronic lung allograft dysfunction in lung transplant patients", Clinical Transplantation, 31: e12898 (2017).
Coghill et al., "Effector CD4+ T cells, the cytokines they generate, and GVHD: something old and something new", Blood, 117(12): 3268-3276 (Mar. 24, 2011).
Cottin, "Eosinophilic lung diseases", Clin Chest Med, 37: 535-556 (2016).
Craiglow et al., "Tofacitinib citrate for the treatment of vitiligo: A pathogenesis-directed therapy", JAMA Dermatology, 151: 1110-1112 (2015).
De La Torre et al., "Salbutamol metabolism how to differentiate oral vs. inhaled administrations: looking outside the box", World Anti-doping Agency (Nov. 20, 2015).

(Continued)

*Primary Examiner* — Charanjit Aulakh

(74) *Attorney, Agent, or Firm* — Jeffrey A. Hagenah; Florence Jovic

(57) ABSTRACT

The invention is directed to a process for preparing compounds which are useful as intermediates for the preparation of medicinal agents having inhibitory activity for JAK.

21 Claims, No Drawings

(56) References Cited

OTHER PUBLICATIONS

De Nitto et al., "Involvement of interleukin-15 and interleukin-21, two gamma-chain-related cytokines, in celiac disease", World J Gastroenterol, 15(37): 4609-4614 (Oct. 7, 2009).
Duffel et al., "On the mechanism of aryl sulfotransferase", J Biological Chemistry, 256(21):11123-11127 (1981).
Eaton et al., "Stereoselective sulphate conjugation of salbutamol by human lung and bronchial epithelial cells", Br J Clin Pharmacol, 41:201-206 (1996).
El-Hashemite et al., "Interferon-gamma-Jak-Stat signaling in pulmonary lymphangioleiomyomatosis and renal angiomyolipoma", Am J Respir Cell Mol Biol, 33: 227-230 (2005).
El-Hashemite et al., "Perturbed IFN-gamma-Jak-signal transducers and activators of transcription signaling in tuberous sclerosis mouse models: Synergistic effects of rapamycin-IFN-gamma treatment", Cancer Research, 64: 3436-3443 (May 15, 2004).
Fang et al., "Interleukin-6-572C/G polymorphism is associated with serum interleukin-6 levels and risk of idiopathic pulmonary arterial hypertension", Journal of the American Society of Hypertension, 11(3): 171-177 (2017).
Feliciani et al., "A TH2-like cytokine response is involved in bullous pemphigoid. The role of IL-4 and IL-5 in the pathogenesis of the disease", International Journal of Immunopathology and Pharmacology, 12(2): 55-61 (1999).
Fenwick et al., "Effect of JAK inhibitors on release of CXCL9, CXCL10 and CXCL11 from human airway epithelial cells", PLOS One, 10(6): e0128757 (2015).
Foloppe et al., "Identification of a buried pocket for potent and selective inhibition of Chk1: Prediction and verification", Bioorganic & Medicinal Chemistry, 14: 1792-1804 (2006).
Funatsu et al., "Association of vitreous inflammatory factors with diabetic macular edema", Ophthalmology, 116: 73-79 (2009).
Gauthier et al., "Update on chronic lung allograft dysfunction", Curr Transplant Rep, 3(3): 185-191 (Sep. 2016).
Horai et al, "Cytokines in autoimmune uveitis", Journal of Interferon & Cytokine Research, 31(10): 733-744 (2011).
Huang et al., "Glycoprotein 130 inhibitor ameliorates monocrotalline-induced pulmonary hypertension in rats", Canadian Journal of Cardiology, 32: 1356.e1-1356.e10 (2016).
Jones et al., "Design and synthesis of a Pan-Janus kinase inhibitor clinical candidate (PF-06263276) suitable for inhaled and topical delivery for the treatment of inflammatory diseases of the lungs and skin", J. Med. Chem., 60: 767-786 (2017).
Knickelbein et al., "Inflammatory mechanisms of age-related macular degeneration", International Ophthalmology Clinics, 55(3): 63-78 (2015).
Kudlacz et al., "The JAK-3 inhibitor CP-690550 is a potent anti-inflammatory agent in a murine model of pulmonary eosinophilia", European Journal of Pharmacology, 582: 154-161 (2008).
Kumawat et al., "Microscopic colitis patients demonstrate a mixed Th17/Tc17 and Th1/Tc1 mucosal cytokine profile", Molecular Immunology, 55: 355-364 (2013).
Malaviya et al., "Janus Kinase-3 dependent inflammatory responses in allergic asthma", International Immunopharmacology, 10: 829-836 (2010).
Matsunaga et al., "Effects of a Janus kinase inhibitor, pyridone 6, on airway responses in a murine model of asthma", Biochemical and Biophysical Research Communications, 404: 261-267 (2011).
Mcbride et al., "Design and structure-activity relationship of 3-benzimidazol-2-yl-1H-indazoles as inhibitors of receptor tyrosine kinases", Bioorganic & Medicinal Chemistry Letters, 16: 3595-3599 (2006).
Mcbride et al., "3-Benzimidazol-2-yl-1H-indazoles as potent c-ABL inhibitors", Bioorganic & Medicinal Chemistry Letters, 16: 3789-3792 (2006).and renal angiomyolipoma, Am J Respir Cell Mol Biol, 33: 227-230 (2005).
Netchiporouk et al., "Deregulation in STAT signaling is important for cutaneous T-cell lymphoma (CTCL) pathogenesis and cancer progression", Cell Cycle, 13(21): 3331-3335 (Nov. 1, 2014).
Okiyama et al., "Reversal of CD8 T-cell-mediated mucocutaneous graft-versus-host-like disease by the JAK inhibitor tofacitinib", Journal of Investigative Dermatology, 134: 992-1000 (2014).
Owen et al., "Soluble mediators of diabetic macular edema: The diagnostic role of aqueous VEGF and cytokine levels in diabetic macular edema", Curr Diab Rep, 13(4): 476-480 (Aug. 2013).
Reimund et al., "Mucosal inflammatory cytokine production by intestinal biopsies in patients with ulcerative colitis and Crohn's disease", Journal of Clinical Immunology, 16(3): 144-150 (1996).
Sharan et al., "Pulmonary metabolism of resveratrol: in vitro and in vivo evidence", Drug Metab Dispos, 41:1163-1169 (May 2013).
Shino et al., "The prognostic importance of CXCR3 chemokine during organizing pneumonia on the risk of chronic lung allograft dysfunction after lung transplantation", PLOS One, 12(7): e0180281 (2017).
Simov et al., "Structure-based design and development of (benz)imidazole pyridones as JAK1-selective kinase inhibitors", Bioorganic & Medicinal Chemistry Letters, 26: 1803-1808 (2016).
Sohn et al., "Changes in aqueous concentrations of various cytokines after intravitreal triamcinolone versus bevacizumab for diabetic macular edema", Ophthalmology, 152: 686-694 (2011).
Sonkoly et al., "IL-31: A new link between T cells and pruritus in atopic skin inflammation", J Allergy Clin Immunol, 117(2): 411-417 (2006).
Stallmach et al., "Cytokine/chemokine transcript profiles reflect mucosal inflammation in Crohn's disease", Int J Colorectal Dis, 19: 308-315 (2004).
Stevenson et al., "Dry eye disease", Arch Ophthalmol, 130(1): 90-100 (Jan. 2012).
The International Search Report and the Written Opinion for PCT/US2019/049338.
Gontcharov et al., "Development of a scalable synthesis for an inhaled pan-JAK inhibitor", Organic Process Research & Development 2019, XXX, XXX-XXX (published online).
Tanaka et al., "New insight into mechanisms of pruritus from molecular studies on familial primary localized cutaneous amyloidosis", British Journal of Dermatology, 161: 1217-1224 (2009).
Trujillo et al., "2-(6-Phenyl-1H-indazol-3-yl)-1H-benzo[d]imidazoles: Design and synthesis of a potent and isoform selective PKC-zeta inhibitor", Bioorganic & Medicinal Chemistry Letters, 19: 908-911 (2009).
Vincenti et al., "Randomized phase 2b trial of tofacitinib (CP-690,550) in de novo kidney transplant patients: Efficacy, renal function and safety at 1 year", American Journal of Transplantation, 12: 2446-2456 (2012).
Ward et al., "Enantiomeric disposition of inhaled, intravenous and oral racemic-salbutamol in man—no evidence of enantioselective lung metabolish", J Clin Pharmacol, 49:15-22 (2000).
Weinbrand-Goichberg et al., "Eosinophilic esophagitis: an immune-mediated esophageal disease", Immunol Res, 56: 249-260 (2013).
Welz-Kubiak et al., "IL-31 is overexpressed in lichen planus but its level does not correlate with pruritus severity", Journal of Immunology Research, Article 854747, 6 pages (2015).
Woywodt et al., "Mucosal cytokine expression, cellular markers and adhesion molecules in inflammatory bowel disease", European Journal of Gastroenterology & Hepatology, 11: 267-276 (1999).
Xing et al., "Alopecia areata is driven by cytotoxic T lymphocytes and is reversed by JAK inhibition", Nature Medicine, 20(9): 1043-1049 (Sep. 2014).
Yamamoto et al., "Mucosal inflammation in the terminal ileum of ulcerative colitis patients: Endoscopic findings and cytokine profiles", Digestive and Liver Disease, 40: 253-259 (2008).
Yan et al., "Discovery of 3-(5'-Substituted)-benzimidazol-5-(1-(3,5-dichloropyridin-4-yl)ethoxy)-1H-indazoles as potent fibroblast growth factor receptor inhibitors: Design, synthesis, and biological evaluation", J. Med. Chem., 59: 6690-6708 (2016).
Yano et al., "Ipilimumab augments antitumor activity of bispecific antibody-armed T cells", Journal of Translational Medicine, 12: 191 (2014).
Zeiser et al., "Ruxolitinib in corticosteroid-refractory graft-versus-host disease after allogeneic stem cell transplantation: a multi-center survey", Leukemia, 29(10): 2062-2068 (Oct. 2015).

(56) References Cited

OTHER PUBLICATIONS

Zhou et al., "Cytokines and Behcet's Disease", Autoimmunity Reviews, 11: 699-704 (2012).
U.S. Appl. No. 16/701,426, Unpubliished, Fatheree et al.
Wilcken et al., "Principles and applications of halogen bonding in medicinal chemistry and chemical biology", Journal of Medicinal Chemistry, 56: 1363-1388 (2013).

PROCESS FOR PREPARING JAK INHIBITORS AND INTERMEDIATES THEREOF

CROSS-REFERENCE TO RELATED APPLICATIONS

This application claims the benefit of U.S. Provisional Application No. 62/726,600, filed on Sep. 4, 2018, the disclosure of which is incorporated herein by reference in its entirety.

BACKGROUND OF THE INVENTION

Field of the Invention

The invention is directed to a process for preparing compounds which are useful as an intermediates for the preparation of medicinal agents. In particular, the invention is directed to the preparation of intermediates to JAK inhibitors.

State of the Art

The JAK family comprises four members, JAK1, JAK2, JAK3, and tyrosine kinase 2 (TYK2). Binding of cytokine to a JAK-dependent cytokine receptor induces receptor dimerization which results in phosphorylation of tyrosine residues on the JAK kinase, effecting JAK activation. Phosphorylated JAKs, in turn, bind and phosphorylate various STAT proteins which dimerize, internalize in the cell nucleus and directly modulate gene transcription, leading, among other effects, to the downstream effects associated with inflammatory disease. The JAKs usually associate with cytokine receptors in pairs as homodimers or heterodimers. Each of the four members of the JAK family is implicated in the signaling of at least one of the cytokines associated with inflammation. Consequently, a chemical inhibitor with pan-activity against all members of the JAK family could modulate a broad range of pro-inflammatory pathways that contribute to lung inflammatory diseases such as severe asthma, COPD, and Chronic Lung Allograft Dysfunction (CLAD). It would therefore be desirable to have an efficient process for preparing specific JAK inhibitors.

SUMMARY OF THE INVENTION

The invention is directed to a process for preparing compounds which are useful as intermediates for the preparation of medicinal agents having inhibitory activity for JAK.

Accordingly, in one aspect, the invention provides a process for preparing a compound of formula J-15, or a salt thereof:

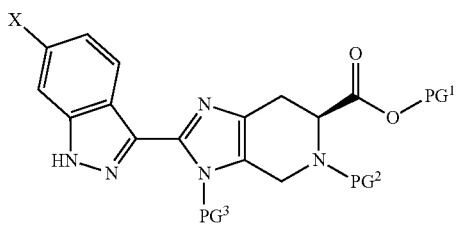

J-15 wherein
X is selected from the group consisting of Br, I and Cl;
$PG^1$ is a carboxylic acid protecting group;
$PG^2$ is an amino protecting group; and
$PG^3$ is an amino protecting group;
the process comprising:
(a) reacting a compound of Formula J-14:

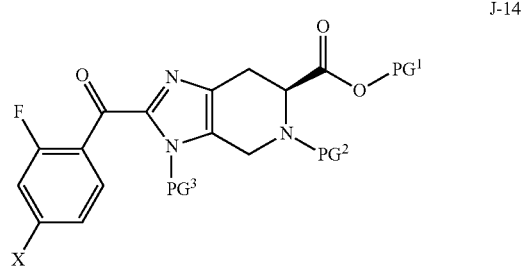

J-14 or a salt thereof, with hydrazine to give the compound of formula J-15 and
(b) optionally forming a salt of compound J-15.

In another aspect, the invention provides a compound of formula J-14:

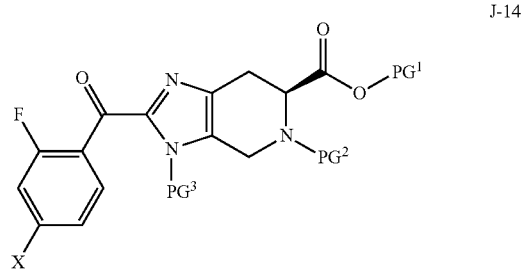

J-14 or a salt thereof, wherein
X is selected from the group consisting of Br, I and Cl;
$PG^1$ is a carboxylic acid protecting group;
$PG^2$ is an amino protecting group; and
$PG^3$ is an amino protecting group.

In another aspect, the invention provides a compound of formula J-15:

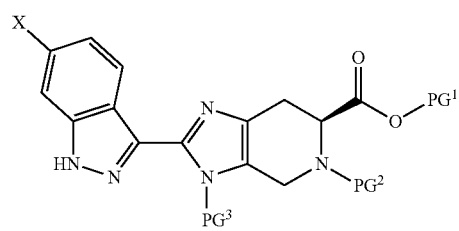

J-15 or a salt thereof,
wherein
X is selected from the group consisting of Br, I and Cl;
$PG^1$ is a carboxylic acid protecting group;
$PG^2$ is an amino protecting group; and
$PG^3$ is an amino protecting group.

In another aspect, the invention provides a process for preparing a compound of formula J-16, or a salt thereof:

J-16 wherein
PG¹ is a carboxylic acid protecting group;
PG² is an amino protecting group;
PG³ is an amino protecting group;
PG⁴ is an hydroxyl protecting group; and
R is H or F;
the process comprising:
(a) reacting a compound of formula J-13:

J-13 wherein X is selected from the group consisting of Br, I and Cl; and Y is a leaving group; with a compound of formula J-11:

J-11 in the presence of a base, to give a compound of formula J-14:

J-14 and optionally forming a salt of compound J-14;
(b) reacting the compound of formula J-14, or a salt thereof, with hydrazine to give a compound of formula J-15:

J-15 and optionally forming a salt of compound J-15;
(c) reacting the compound of Formula J-15, or a salt thereof, with a compound of formula J-5, J-6 or J-7:

J-5

J-6

J-7 wherein $R^a$ and $R^b$ are each independently selected from $C_{1-8}$ alkyl, wherein $R^a$ and $R^b$ may optionally be joined to form a 4 to 8 membered ring; in the presence of a base, a palladium catalyst and a phosphine ligand to give the compound of formula J-16, and optionally forming a salt of compound J-16.

DETAILED DESCRIPTION OF THE INVENTION

In one aspect, the invention provides a process for preparing a compound of formula J-15, or a salt thereof:

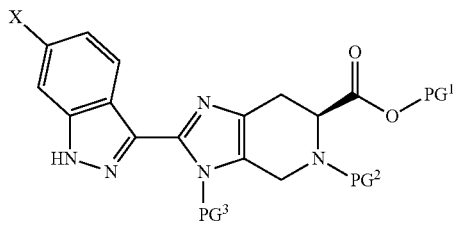

J-15 wherein
X is selected from the group consisting of Br, I and Cl;
PG$^1$ is a carboxylic acid protecting group;
PG$^2$ is an amino protecting group; and
PG$^3$ is an amino protecting group;
the process comprising:
(a) reacting a compound of Formula J-14:

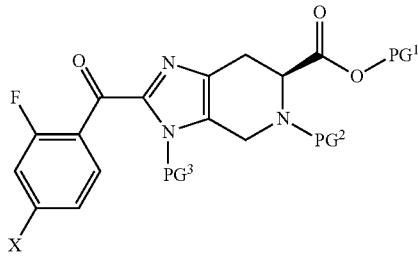

J-14 or a salt thereof, with hydrazine to give the compound of formula J-15 and
(b) optionally forming a salt of compound J-15.

In some aspects, the reaction with hydrazine is conducted at about 60° C. In some aspects, the reaction with hydrazine is conducted at 60° C.±20° C.

In some aspects, X is selected from the group consisting of Br, I and Cl; PG$^1$ is an alkyl or benzyl group wherein the benzyl group is optionally substituted; PG$^2$ is selected from the group consisting of an acyl group, an alkoxycarbonyl group, an arylmethyl group, and a silyl group; and PG$^3$ is selected from the group consisting of an acyl group, an alkoxycarbonyl group, an arylmethyl group, and a silyl group.

In some aspects, X is Br. In some aspects, X is Br, PG$^1$ is benzyl, PG$^2$ is tert-butoxycarbonyl and PG$^3$ is benzyl.

In some aspects, compound J-14, or a salt thereof, is prepared by:
(a) reacting a compound of formula J-13:

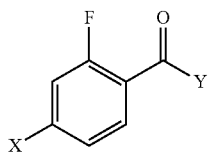

J-13 wherein Y is a leaving group, with a compound of formula J-11:

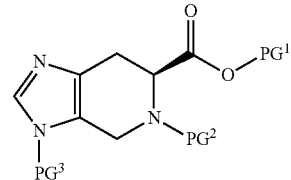

J-11 in the presence of a base, to give J-14, and
(b) optionally forming a salt of compound J-14.

In some aspects, Y is Cl.

In another aspect, the invention provides a compound of formula J-14:

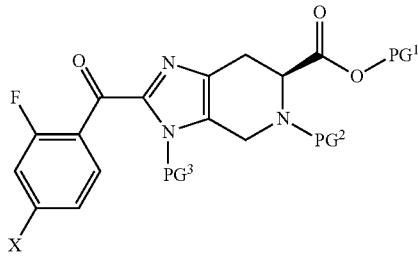

J-14 or a salt thereof, wherein
X is selected from the group consisting of Br, I and Cl;
PG$^1$ is a carboxylic acid protecting group;
PG$^2$ is an amino protecting group; and
PG$^3$ is an amino protecting group.

In some aspects, X is selected from the group consisting of Br, I and Cl; PG$^1$ is an alkyl or benzyl group wherein the benzyl group is optionally substituted; PG$^2$ is selected from the group consisting of an acyl group, an alkoxycarbonyl group, an arylmethyl group, and a silyl group; and PG$^3$ is selected from the group consisting of an acyl group, an alkoxycarbonyl group, an arylmethyl group, and a silyl group.

In another aspect, the invention provides a compound of formula I-14:

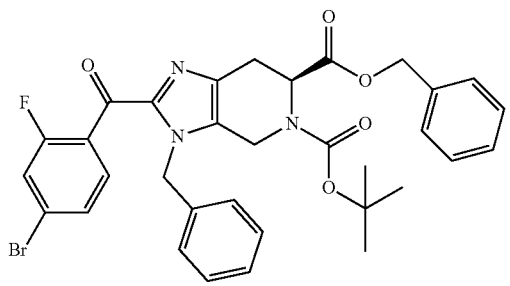

I-14 or a salt thereof.

In another aspect, the invention provides a compound of formula J-15:

J-15
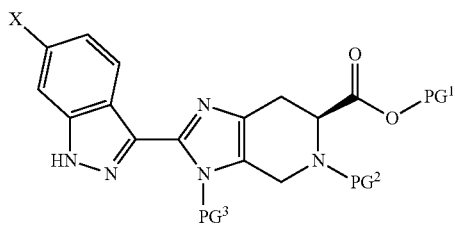

or a salt thereof,
wherein
X is selected from the group consisting of Br, I and Cl;
PG¹ is a carboxylic acid protecting group;
PG² is an amino protecting group; and
PG³ is an amino protecting group.

In some aspects, X is selected from the group consisting of Br, I and Cl; PG¹ is an alkyl or benzyl group wherein the benzyl group is optionally substituted; PG² is selected from the group consisting of an acyl group, an alkoxycarbonyl group, an arylmethyl group, and a silyl group; and PG³ is selected from the group consisting of an acyl group, an alkoxycarbonyl group, an arylmethyl group, and a silyl group.

In another aspect, the invention provides a compound of formula I-15:

I-15
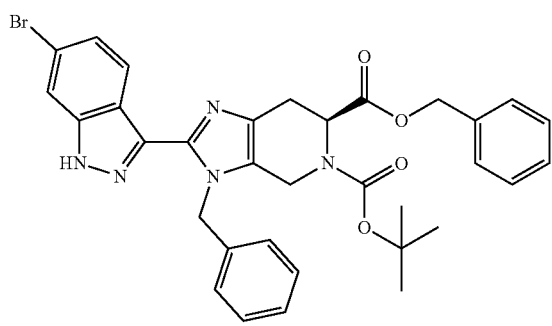

or a salt thereof.

In another aspect, the invention provides a process for preparing a compound of formula J-16, or a salt thereof:

J-16
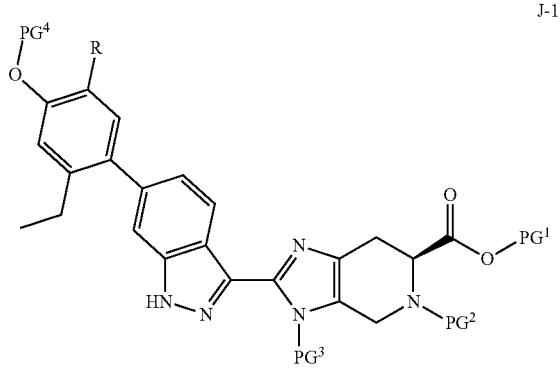

wherein
PG¹ is a carboxylic acid protecting group;
PG² is an amino protecting group;
PG³ is an amino protecting group;
PG⁴ is an hydroxyl protecting group; and
R is H or F;
the process comprising:
(a) reacting a compound of formula J-13:

J-13
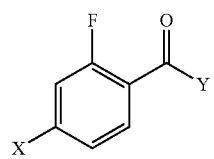

wherein X is selected from the group consisting of Br, I and Cl; and Y is a leaving group; with a compound of formula J-11:

J-11
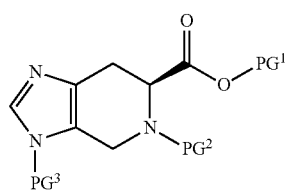

in the presence of a base, to give a compound of formula J-14:

J-14
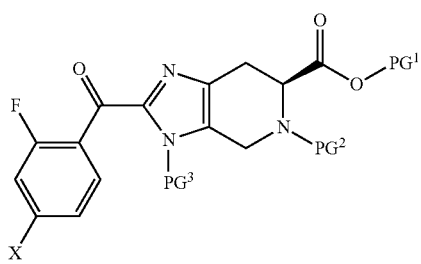

and optionally forming a salt of compound J-14;
(b) reacting the compound of formula J-14, or a salt thereof, with hydrazine to give a compound of formula J-15:

J-15
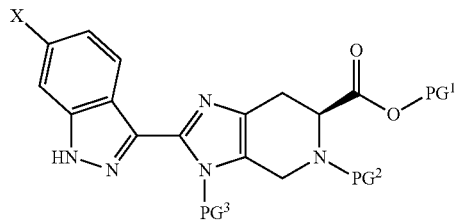

and optionally forming a salt of compound J-15;

(c) reacting the compound of Formula J-15, or a salt thereof, with a compound of formula J-5, J-6 or J-7:

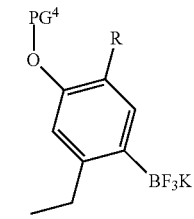

J-5

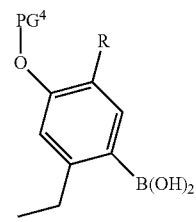

J-6

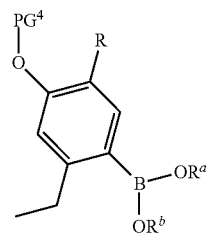

J-7 wherein $R^a$ and $R^b$ are each independently selected from $C_{1-8}$ alkyl, wherein $R^a$ and $R^b$ may optionally be joined to form a 4 to 8 membered ring; in the presence of a base, a palladium catalyst and a phosphine ligand to give the compound of formula J-16, and optionally forming a salt of compound J-16.

In some aspects, step (c) is conducted in the presence of a diboron reagent. In some aspects, step (c) is conducted in the presence of tetrahydroxydiboron or a diboronic ester. In some embodiments, the catalyst is the product of the reaction of bis(pinacolato)diboron with potassium fluoride hydrofluoride. In some embodiments, the catalyst is obtained by reacting bis(pinacolato)diboron in propan-2-ol with potassium fluoride hydrofluoride in water followed by filtration and drying of the solids obtained.

In some aspects, the reaction with hydrazine in step (b) is conducted at 60° C.±20° C.

In some aspects, X is selected from the group consisting of Br, I and Cl; $PG^1$ is an alkyl or benzyl group wherein the benzyl group is optionally substituted; $PG^2$ is selected from the group consisting of an acyl group, an alkoxycarbonyl group, an arylmethyl group, and a silyl group; $PG^3$ is selected from the group consisting of an acyl group, an alkoxycarbonyl group, an arylmethyl group, and a silyl group; $PG^4$ is selected from the group consisting of a silyl group, an acyl group, and an arylmethyl group. In some aspects, X is Br. In some aspects, X is Br, $PG^1$ is benzyl, $PG^2$ is tert-butoxycarbonyl $PG^3$ is benzyl, and $PG^4$ is benzyl.

In some aspects, Y is Cl.

In some aspects, the palladium catalyst and phosphine ligand of step (c) are bis(di-tert-butyl(4-dimethylaminophenyl)phosphine)dichloropalladium(II).

In the present process, compound J-13:

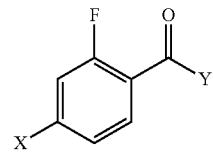

J-13 is reacted with a compound of formula J-11:

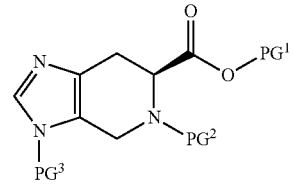

J-11 in the presence of a base, to give a compound of formula J-14:

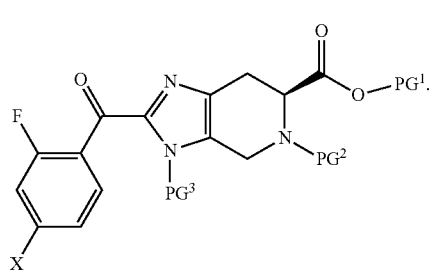

J-14

Typically, the reaction is conducted in a solvent such as acetonitrile in the presence of an excess (for example 3 to 7 equivalents) of a base such as trimethylamine. One to two equivalents of J-13 is typically used.

In the present process, compound J-14, or a salt thereof, is reacted with hydrazine to give a compound of formula J-15:

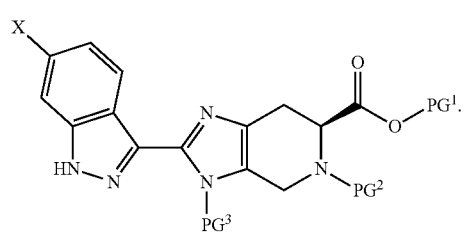

J-15

Typically, the reaction is conducted in a solvent such as THF and an excess of hydrazine is used, for example between 2 and 10 equivalents. The reaction is heated at about 60° C. until completion, typically between 0.5 and 6 hours.

In the present process, compound J-15, or a salt thereof, is reacted with a compound of formula J-5, J-6 or J-7:

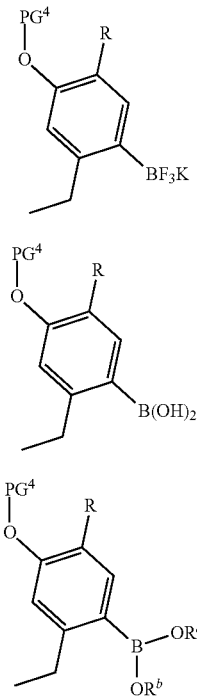

J-5

J-6

J-7 in the presence of a base, a palladium catalyst and a phosphine ligand to give the compound of formula J-16:

J-16

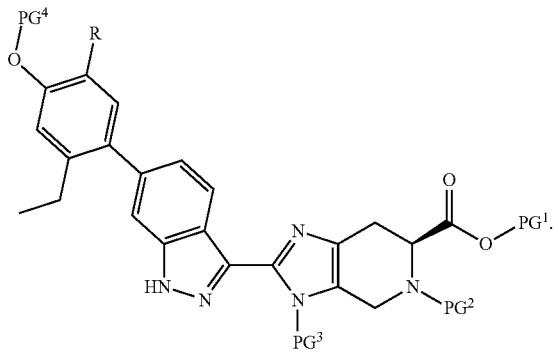

The reaction is typically conducted by contacting J-16 with between about 1 and about 1.5 equivalents of J-5, J-6 or J-7 in the presence of a catalytic amount of a palladium catalyst and phosphine ligand (between about 0.005 and about 0.1 equivalents), and between about 2 and about 6 equivalents of a base. Conducting the reaction in the presence of an additional catalyst increases the yield of product J-16. The additional catalyst may be a diboron reagent. The additional catalyst may be tetrahydroxydiboron, a diboronic ester or the product of the reaction of bis(pinacolato)diboron with potassium fluoride hydrofluoride, as illustrated in Preparation 4.

Suitable palladium catalysts include bis(di-tert-butyl(4-dimethylaminophenyl)phosphine)dichloropalladium(II), tris (dibenzylideneacetone)dipalladium(0) ($Pd_2dba_3$), palladium (II) acetate ($Pd(OAc)_2$), dichloro(1,1'-bis(diphenylphosphino)-ferrocene)dipalladium(II) ($Pd(dppf)Cl_2$), dichloro bis(triphenylphosphine)-palladium(II) ($Pd(PPh_3)_2Cl_2$), and the like, where the common abbreviations are given in parentheses. Phosphine ligands useful in the present reaction include tricyclohexylphosphine ($PCy_3$), tricyclohexylphosphine tetrafluoroborate ($PCy_3HBF_4$), 1,1'-bis(diphenylphosphino)-ferrocene (dppf), 1,1'-bis(di-tert-butylphosphino)ferrocene, tri(2-furyl)phosphine, 1,3-bis(diphenylphosphino) propane (dppp), 1,5-bis(diphenylphosphino)pentane (dpppe), tri-tert-butylphosphine ($P(t-Bu)_3$), and 9,9-dimethyl-4,5-bis(diphenylphosphino)xanthene (Xantphos).

Typical bases for the coupling reaction include potassium fluoride, cesium carbonate, and cesium fluoride. Alternatively, sodium carbonate, potassium carbonate, sodium acetate, potassium tert-butoxide, 1,8-diazabicyclo[5.4.0]undec-7-ene (DBU), or 1,4-diazabicyclo[2.2.2]octane (DABCO) can be used for the base. The reaction is typically conducted in an inert diluent, such as tetrahydrofuran, N,N-dimethylformamide, N,N-dimethyacetamide, or N-methylpyrrolidone. Suitable mixed solvent systems include tetrahydrofuran and water, tetrahydrofuran and N,N-dimethylformamide, tetrahydrofuran and N-methylpyrrolidone, acetone and water, ethanol and water, and isopropanol and water. The reaction is typically conducted at a temperature of between about 40 and about 120° C. for about 1 to about 20 hours or until the reaction is substantially complete. The product J-16 is isolated as a solid by conventional procedures.

Definitions

When describing this invention including its various aspects and embodiments, the following terms have the following meanings, unless otherwise indicated.

The term "alkyl" means a monovalent saturated hydrocarbon group which may be linear or branched or combinations thereof. Unless otherwise defined, such alkyl groups typically contain from 1 to 10 carbon atoms. Representative alkyl groups include, by way of example, methyl (Me), ethyl (Et), n-propyl (n-Pr) or (nPr), isopropyl (i-Pr) or (iPr), n-butyl (n-Bu) or (nBu), sec-butyl, isobutyl, tert-butyl (t-Bu) or (tBu), n-pentyl, n-hexyl, 2,2-dimethylpropyl, 2-methylbutyl, 3-methylbutyl, 2-ethylbutyl, 2,2-dimethylpentyl, 2-propylpentyl, and the like.

When a specific number of carbon atoms are intended for a particular term, the number of carbon atoms is shown preceding the term. For example, the term "$C_{1-3}$ alkyl" means an alkyl group having from 1 to 3 carbon atoms wherein the carbon atoms are in any chemically-acceptable configuration, including linear or branched configurations.

The term "cycloalkyl" means a monovalent saturated carbocyclic group which may be monocyclic or multicyclic. Unless otherwise defined, such cycloalkyl groups typically contain from 3 to 10 carbon atoms. Representative cycloalkyl groups include, by way of example, cyclopropyl (cPr), cyclobutyl (cBu), cyclopentyl, cyclohexyl, cycloheptyl, cyclooctyl, adamantyl, and the like.

The term "cpropyl" means cyclopropyl.

The term "heterocyclyl", "heterocycle", "heterocyclic", or "heterocyclic ring" means a monovalent saturated or partially unsaturated cyclic non-aromatic group, having from 3 to 10 total ring atoms, wherein the ring contains from 2 to 9 carbon ring atoms and from 1 to 4 ring heteroatoms selected from nitrogen, oxygen, and sulfur. Heterocyclic groups may be monocyclic or multicyclic (i.e., fused or bridged). Representative heterocyclyl groups include, by way of example, pyrrolidinyl, piperidinyl, piperazinyl, imidazolidinyl, morpholinyl, thiomorpholyl, indolin-3-yl, 2-imidazolinyl, tetrahydropyranyl, 1,2,3,4-tetrahydroisoquinolin-2-yl, quinuclidinyl, 7-azanorbornanyl, nortropanyl, and the like, where the point of attachment is at any available carbon or nitrogen ring atom. Where the context makes the point of attachment of the heterocyclic group evident, such groups may alternatively be referred to as a non-valent species, i.e. pyrrolidine, piperidine, piperazine, imidazole, tetrahydropyran etc.

The term "halo" means fluoro, chloro, bromo or iodo.

The term "therapeutically effective amount" means an amount sufficient to effect treatment when administered to a patient in need of treatment.

The term "treating" or "treatment" means preventing, ameliorating or suppressing the medical condition, disease or disorder being treated (e.g., a respiratory disease) in a patient (particularly a human); or alleviating the symptoms of the medical condition, disease or disorder.

The term "pharmaceutically acceptable salt" means a salt that is acceptable for administration to a patient or a mammal, such as a human (e.g., salts having acceptable mammalian safety for a given dosage regime). Representative pharmaceutically acceptable salts include salts of acetic, ascorbic, benzenesulfonic, benzoic, camphorsulfonic, citric, ethanesulfonic, edisylic, fumaric, gentisic, gluconic, glucoronic, glutamic, hippuric, hydrobromic, hydrochloric, isethionic, lactic, lactobionic, maleic, malic, mandelic, methanesulfonic, mucic, naphthalenesulfonic, naphthalene-1,5-disulfonic, naphthalene-2,6-disulfonic, nicotinic, nitric, orotic, pamoic, pantothenic, phosphoric, succinic, sulfuric, tartaric, p-toluenesulfonic and xinafoic acid, and the like.

The term "salt thereof" means a compound formed when the hydrogen of an acid is replaced by a cation, such as a metal cation or an organic cation and the like. For example, the cation can be a protonated form of a compound, i.e. a form where one or more amino groups have been protonated by an acid. Typically, the salt is a pharmaceutically acceptable salt, although this is not required for salts of intermediate compounds that are not intended for administration to a patient.

The term "amino protecting group" means a protecting group suitable for preventing undesired reactions at an amino nitrogen. Representative amino-protecting groups include, but are not limited to, formyl; acyl groups, for example alkanoyl groups, such as acetyl and tri-fluoroacetyl; alkoxycarbonyl groups, such as tert-butoxycarbonyl (Boc); arylmethoxycarbonyl groups, such as benzyloxycarbonyl (Cbz), 9-fluorenylmethoxycarbonyl (Fmoc), p-nitrobenzyloxycarbonyl (PNZ), 2,4-dichlorobenzyloxycarbonyl, and 5-benzisoxazolylmethoxycarbonyl; arylmethyl groups, such as benzyl (Bn), 4-methoxybenzyl, trityl (Tr), and 1,1-di-(4'-methoxyphenyl)methyl; silyl groups, such as trimethylsilyl (TMS), tert-butyldimethylsilyl (TBDMS), [2-(trimethylsilyl)ethoxy]methyl (SEM); and the like.

The term "carboxylic acid protecting group" means a protecting group suitable for preventing undesired reactions at a carboxylic acid. Representative carboxylic acid-protecting groups include, but are not limited to, esters, such as methyl, ethyl, tert-butyl, benzyl (Bn), p-methoxybenzyl (PMB), 9-fluorenylmethyl (Fm), trimethylsilyl (TMS), tert-butyldimethylsilyl (TBS, TBDMS), diphenylmethyl (benzhydryl, DPM), and the like.

The term "hydroxyl protecting group" means a protecting group suitable for preventing undesirable reactions at a hydroxyl group. Representative hydroxyl protecting groups include, but are not limited to, silyl groups including tri($C_{1-6}$ alkyl)silyl groups, such as trimethylsilyl (TMS), triethylsilyl (TES), tert-butyldimethylsilyl (TBS) and the like; esters (acyl groups) including $C_{1-6}$ alkanoyl groups, such as formyl, acetyl and the like; arylmethyl groups, such as benzyl (Bn), p-methoxybenzyl (PMB), 9-fluorenylmethyl (Fm), diphenylmethyl (benzhydryl, DPM) and the like.

Numerous protecting groups, and their introduction and removal, are described in T. W. Greene and P. G. M. Wuts, Protecting Groups in Organic Synthesis, Third Edition, Wiley, New York

EXAMPLES

The following synthetic examples are offered to illustrate the invention, and are not to be construed in any way as limiting the scope of the invention. In the examples below, the following abbreviations have the following meanings unless otherwise indicated. Abbreviations not defined below have their generally accepted meanings.

ACN=acetonitrile
DMF=N,N-dimethylformamide
EtOAc=ethyl acetate
EtOH=ethanol
NaHMDS=sodium bis(trimethylsilyl)amide
MeTHF=2-methyltetrahydrofuran
MTBE=tert-butyl methyl ether
psi=pounds per square inch
Rt=retention time Reagents and solvents were purchased from commercial suppliers (Aldrich, Strem Chemicals, Inc., etc.), and used without further purification. Progress of reaction mixtures was monitored by analytical high performance liquid chromatography and mass spectrometry. Endo/exo ratios of products were determined by HPLC analysis using the protocols described below. Reaction mixtures were worked up as described specifically in each reaction; commonly they were purified by extraction and other purification methods such as temperature-, and solvent-dependent crystallization, and precipitation. Characterization of reaction products was routinely carried out by mass and $^1$H-NMR spectrometry. For NMR measurement, samples were dissolved in deuterated solvent (DMSO-$d_6$ or CDCl$_3$), and $^1$H-NMR spectra were acquired with a Varian Gemini 2000 instrument (400 MHz) under standard observation conditions. Mass spectrometric identification of compounds was performed using an Agilent (Palo Alto, Calif.) model 1100 LC/MSD instrument.

General HPLC Conditions
Column: Zorbax SB-Aq, 5 μm. 4.6×250 mm
Column temperature: 40° C.
Flow rate: 1.0 mL/min
Mobile Phases: A=Water/ACN (98:2)+0.1% TFA
B=Water/ACN (10:90)+0.1% TFA,
Injection volume: 10 μL
Detector wavelength: 214 nm HPLC Method 1
Crude compounds were dissolved in Water/ACN (50:50) at about 1 mg/mL and analyzed using the following gradient over 20 min (time (min)/% B): 0/10, 2.5/20, 9/75, 15/90, 17/90, 18/10, 20/10.

HPLC Method 2
Compounds were dissolved in Water/ACN (90:10) at about 1 mg/mL and analyzed using the following gradient over 30 min (time (min)/% B): 0/10, 13/10, 23/65, 28/90, 29/90, 30/10.

HPLC Method 3

Compounds were dissolved in Water/ACN (90:10) at about 1 mg/mL and analyzed using the following gradient over 55 min (time (min)/% B): 0/10, 10/20, 46/75, 47/90, 50/10, 55/10.

Preparation 1: 4-(benzyloxy)-2-ethylphenyl)trifluoro-$\lambda^4$-borane, Potassium Salt I-5

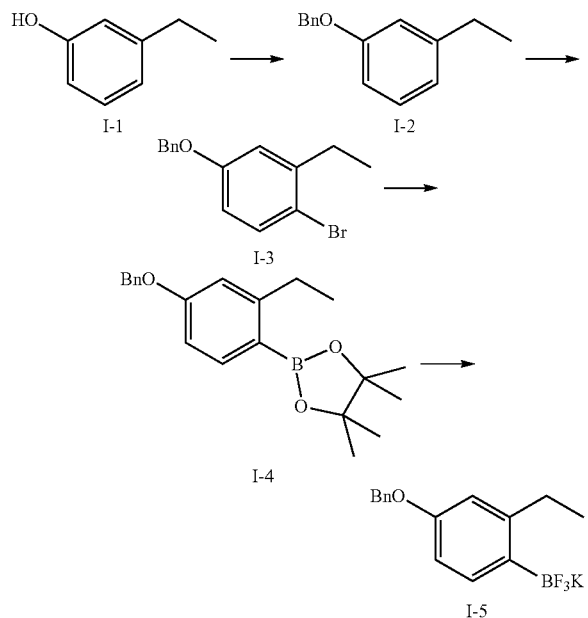

(a) 1-(benzyloxy)-3-ethylbenzene (I-2)

To a stirred solution of 3-ethylphenol (I-1) (25.0 g, 204.0 mmol) in ACN (250 mL, 10 vol) was added potassium carbonate (42.0 g, 306 mmol) at room temperature. The resulting reaction mass was stirred at room temperature for 15 minutes, followed by the addition of benzyl bromide (24.0 mL, 204 mmol) in drop wise manner. The resulting reaction mixture was stirred for 6 hours at room temperature. After completion of the reaction (TLC monitoring), the resulting reaction mass was poured into water (1.0 L) followed by the extraction of compound with EtOAc (2×2 L). The combined organics were washed with cold water, brine solution and dried over sodium sulfate, filtered and evaporated under reduced pressure. The crude product was then purified by column chromatography over silica gel (100-200M) by using eluents 2% EtOAc in hexane to get the desired product (I-2) as a light yellow oily compound (35.0 g, 81%). $^1$H NMR (400 MHz, chloroform-d) δ 7.46-7.44 (m, 2H), 7.39 (t, J=7.6 Hz, 2H), 7.34-7.31 (m, 1H), 7.21 (t, J=7.6 Hz), 6.86-6.80 (m, 3H), 5.07 (s, 2H), 2.64 (q, J=7.6 Hz, 2H), 1.24 (t, J=7.6 Hz, 3H).

(b) 4-(benzyloxy)-1-bromo-2-ethylbenzene (I-3)

To an ice cold stirred solution of 1-(benzyloxy)-3-ethylbenzene (I-2) (35.0 g, 164 mmol) in ACN (525 mL, 15 vol) was added N-bromosuccinimide (32.0 g 181 mmol) in portions over a period of 15 minutes. The resulting reaction mixture was stirred for 1 hour at room temperature. After completion of reaction (TLC monitoring), the resulting reaction mass was poured into ice cold water (1.50 L) followed by the extraction of compound with EtOAc (2×1 L). The combined organics were washed with water and dried over sodium sulfate, filtered and evaporated under reduced pressure to obtain the crude product. n-Hexane (250 mL) was added to the crude material, resulting in a slurry, followed by filtration through a sintered funnel. The mother liquor was evaporated under reduced pressure to obtain the desired product I-3 as a light yellow oily compound (42.0 g, 87%). $^1$H NMR (400 MHz, chloroform-d) δ 7.52-7.29 (m, 7H), 6.88 (s, 1H), 6.68 (d, J=6.0 Hz, 1H), 5.04 (s, 2H), 2.69 (q, J=7.6 Hz, 2H), 1.20 (t, J=7.5 Hz, 3H).

(c) 2-(4-(benzyloxy)-2-ethylphenyl)-4,4,5,5-tetramethyl-1,3,2-dioxaborolane (I-4)

A stirred solution of 4-(benzyloxy)-1-bromo-2-ethylbenzene (I-3) (42.0 g, 144 mmol), bis(pinacolato) diboron (44.0 g, 173 mmol), and potassium acetate (28 g, 288 mmol) in dioxane (440 mL) was degassed by purging N$_2$ (g) for 15 min followed by addition of PdCl$_2$(dppf). DCM complex (11.0 g, 15 mmol). The resulting reaction mixture was heated up to 80° C. for 16 h. After completion of the reaction (TLC monitoring), the reaction mass was filtered through celite bed and the mother liquor was evaporated under reduced pressure to obtain the crude product. The crude residue was purified by column chromatography over silica gel (100-200M) by using eluents 1% EtOAc in hexane to get the desired product (I-4) as a light yellow oily compound (32.0 g, 66%). $^1$H NMR (400 MHz, chloroform-d) δ 7.74 (d, J=8.4 Hz, 1H), 7.45-7.36 (m, 5H), 6.84-6.78 (m, 2H), 5.08 (s, 2H), 2.91 (q, J=7.6 Hz), 1.33 (s, 12H), 1.19 (t, J=7.6 Hz, 3H).

(d) (4-(benzyloxy)-2-ethylphenyl)trifluoro-$\lambda^4$-borane, Potassium Salt (I-5)

To a stirred solution of compound 2-(4-(benzyloxy)-2-ethylphenyl)-4,4,5,5-tetramethyl-1,3,2-dioxaborolane (I-4) (20 g, 59.0 mmol), in acetone:methanol (200 mL, 1:1 ratio, 10 vol), was added a 3M solution of potassium hydrogen fluoride (23.0 g, 295 mmol, dissolved in 98.0 mL of water). The resulting reaction mixture was stirred at room temperature for 16 hours. After completion of the reaction (TLC monitoring), the resulting reaction mass was evaporated under reduced pressure. The solid thus obtained was taken up in water (100 mL) and stirred at room temperature for 30 min. The resulting reaction mass was filtered through a sintered funnel, washed with n-hexane and dried under reduced pressure to provide the desired product (I-5) as a white solid (14.0 g, 74%). $^1$H NMR (400 MHz, chloroform-d) δ 7.43 (d, J=7.2 Hz, 2H), 7.37 (t, J=7.5 Hz, 2H), 7.30 (t, J=7.1 Hz, 1H), 7.22 (d, J=8.0 Hz), 6.58 (s, 1H), 6.53 (d, J=7.9 Hz, 1H), 5.00 (s, 2H), 2.65 (q, J=7.5 Hz, 2H), 1.07 (t, J=7.4 Hz, 3H).

Preparation 2: 6-benzyl 5-(tert-butyl) (S)-3-benzyl-3,4,6,7-tetrahydro-5H-imidazo[4,5-c]pyridine-5,6-dicarboxylate (I-11)

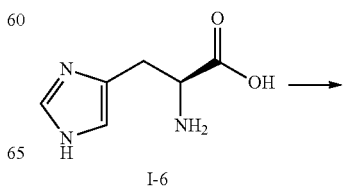

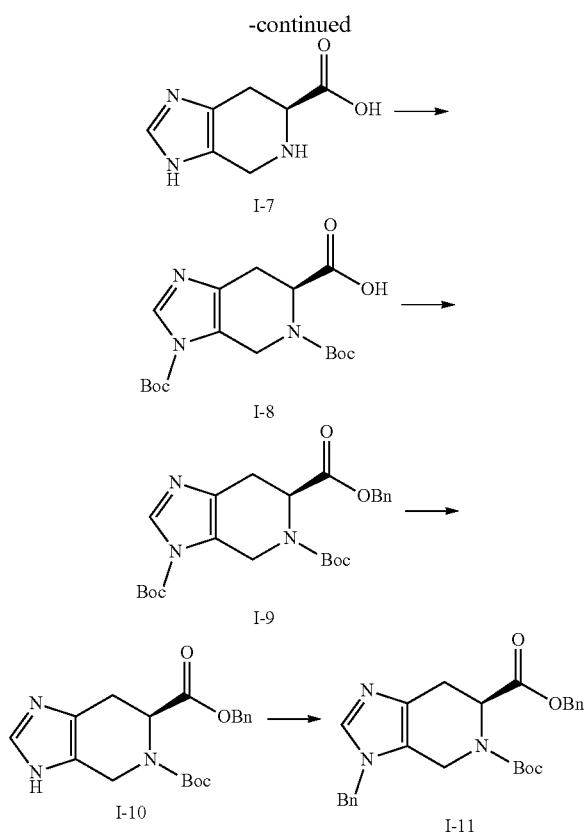

(a) (S)-4,5,6,7-tetrahydro-3H-imidazo[4,5-c]pyridine-6-carboxylic Acid, Hydrochloride Salt (I-7)

To an ice cold stirred suspension of L-histidine (I-6) (5.0 kg, 32.14 mol) in water (40 L, 8 vol.) was added concentrated hydrochloric acid (3.93 L, 33.75 mol), followed by the addition of formaldehyde (5.50 L, 67.5 mol, 37% aq. solution) in drop wise manner. The resulting solution was stirred for 30 minute at same temperature and then heated at 80° C. for 8 hours. Reaction progress was monitored by LCMS. Water was removed under reduced pressure to obtain the crude product, and the resulting crude was stirred for 2 hours in Toluene (20 L). Organics were removed under reduced pressure to remove excess water and the compound was azeotropically dried. The resulting material was then taken in diethyl ether (20 L) and stirred for 2 hours. The solid material was then filtered and air dried to obtain the desired product (I-7) as an off-white solid (6.50 Kg, 85%). $^1$H NMR (400 MHz, D$_2$O) δ 8.69 (s, 1H), 4.56 (d, J=15.4 Hz, 1H), 4.42 (d, J=15.5 Hz, 1H), 4.20 (dd, J=5.5, 5.2 Hz, 1H), 3.42 (dd, J=5.0, 17.0 Hz, 1H), 3.11 (dd, J=10.2, 16.8 Hz, 1H).

(b) (S)-3,5-bis(tert-butoxycarbonyl)-4,5,6,7-tetrahydro-3H-imidazo[4,5-c]pyridine-6-carboxylic Acid (I-8)

To an ice cold stirred solution of (S)-4,5,6,7-tetrahydro-3H-imidazo[4,5-c]pyridine-6-carboxylic acid di-hydrochloride (I-7) (6.10 Kg, 25.40 mol) in 1,4-dioxane (48 L, 8 vol) and water (48 L, 8 vol) was added triethylamine (12.36 L, 89 mol) drop wise followed by the addition of di-tert-butyl dicarbonate (18.07 L, 78.74 mol, dissolved in 5 L of 1,4-dioxane) over a period of 30 min. The resulting reaction mixture was stirred at room temperature for 16 hours. After completion of the reaction (TLC & LCMS monitoring), the yellowish reaction mixture was diluted with water (10 L) and washed successively with diethyl ether (2×10 L) and EtOAc (2×7.50 L). The organic phase was discarded. The aqueous layer was cooled and brought to pH ~3 with 6N HCl solution; the aqueous phase was extracted with EtOAc (3×10 L). The combined organics were washed with brine solution, dried over sodium sulfate, and concentrated under reduced pressure. The oily residue was crystallized from 30% EtOAc:Hexanes to afford the desired product (I-8) as off-white solid (5.1 Kg, 55%). (m/z): [M+H]+ calcd for C$_{17}$H$_{25}$N$_3$O$_6$ 368.18 found 368.21.

(c) 6-benzyl 3,5-di-tert-butyl (S)-6,7-dihydro-3H-imidazo[4,5-c]pyridine-3,5,6(4H)-tricarboxylate (I-9)

To an ice cold solution of (S)-3,5-bis(tert-butoxycarbonyl)-4,5,6,7-tetrahydro-3H-imidazo[4,5-c]pyridine-6-carboxylic acid (I-8) (5.1 Kg, 13.88 mol) in DCM (51 L, 10 vol) was added sequentially saturated aqueous sodium bicarbonate (41.0 L, 8 vol), tetra-butyl ammonium iodide (5.13 Kg, 13.88 mol) and benzyl bromide (2.47 L, 20.82 mol). The resulting reaction mixture was stirred at room temperature for 16 hours. After completion of the reaction (TLC & LCMS monitoring), the biphasic solution was separated. The aqueous layer was extracted with DCM (3×10 L). The combined organics were washed with brine solution, dried over sodium sulfate, filtered, and concentrated under reduced pressure to obtain the crude product, which was purified by column chromatography through silica gel (100-200M) by using eluents 40% EtOAc in hexane to get the desired product (I-9) as viscous oil (4.50 Kg, 72%). (m/z): [M+H]+ calcd for C$_{24}$H$_{31}$N$_3$O$_6$ 458.22 found 458.60.

(d) 6-benzyl 5-(tert-butyl) (S)-3,4,6,7-tetrahydro-5H-imidazo[4,5-c]pyridine-5,6-dicarboxylate (I-10)

To an ice cold solution of 6-benzyl 3,5-di-tert-butyl (S)-6,7-dihydro-3H-imidazo[4,5-c]pyridine-3,5,6(4H)-tricarboxylate (I-9) (4.50 Kg, 9.84 mol) in IPA (45 L, 10 vol) was added ammonium hydroxide (36 L, 8 vol) drop wise. The resulting reaction mixture was further stirred at room temperature for the next 16 hours. After completion of the reaction (TLC & LCMS monitoring), the resulting mixture was diluted with water (25 L) followed by extraction with EtOAc (3×20 L). The combined organics were washed with brine solution, dried over sodium sulfate, filtered and concentrated under reduced pressure to yield the crude product which was purified by column chromatography through silica gel (100-200M) by using eluents 2% MeOH in DCM to obtain the desired product (I-10) as a thick viscous oil (2.70 Kg, 77%). (m/z): [M+H]+ calcd for C$_{19}$H$_{23}$N$_3$O$_4$ 358.17 found 358.33.

(e) 6-benzyl 5-(tert-butyl) (S)-3-benzyl-3,4,6,7-tetrahydro-5H-imidazo[4,5-c]pyridine-5,6-dicarboxylate (I-11)

To an ice cold solution of 6-benzyl 5-(tert-butyl) (S)-3,4,6,7-tetrahydro-5H-imidazo[4,5-c]pyridine-5,6-dicarboxylate (I-10) (2.70 kg, 7.55 mol) in DCM (32.4 L, 12 vol) was added aqueous 1N sodium hydroxide (24.3 L, 9 vol) followed by the sequential addition of tetra-butyl ammonium iodide (2.80 Kg, 7.55 mol) and benzyl bromide (0.99 L, 8.31 mol). The resulting reaction mixture was stirred at room temperature for 2 hours. After completion of the reaction (TLC & LCMS monitoring), the biphasic solution was separated. The aqueous layer was extracted with DCM (3×10 L). The combined organics were washed with brine solution, dried over sodium sulfate, filtered, and concentrated under reduced pressure to yield the crude product which was purified by column chromatography over silica gel (100-200M) by using eluents 40% EtOAc in hexane to obtain the desired product (I-11) as a viscous oil (1.70 Kg, 63%). (m/z): [M+H]+ calcd for $C_{26}H_{29}N_3O_4$ 448.22 found 448.20.

Preparation 3: 6-benzyl 5-(tert-butyl) (S)-3-benzyl-2-(6-bromo-1H-indazol-3-yl)-3,4,6,7-tetrahydro-5H-imidazo[4,5-c]pyridine-5,6-dicarboxylate (I-15)

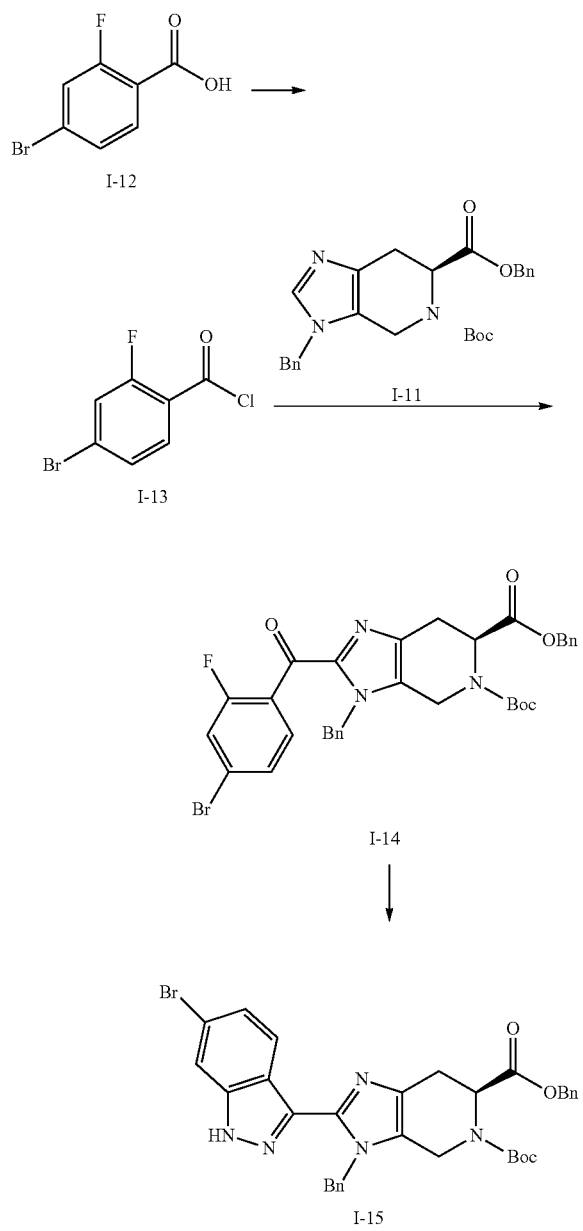

(a) 4-bromo-2-fluorobenzoyl Chloride (I-13)

To an ice cold stirred solution of 4-bromo-2-fluorobenzoic acid (I-12) (1.25 Kg, 5.71 mol) in DCM (12.5 L, 15 vol), was added oxalyl chloride (0.98 L, 11.42 mol) in a drop wise manner. The resulting reaction mixture was stirred for 10 min at the same temperature. DMF (150 mL) was then added in a drop wise manner to the reaction mixture. The resulting reaction mass was allowed to warm to room temperature and stirred for 2 hours. After completion of the reaction (by TLC monitoring), excess oxalyl chloride was removed under reduced pressure under a nitrogen atmosphere to obtain the crude product (I-13) (1.08 Kg, 80%), which was used in the next step without further purification.

(b) 6-benzyl 5-(tert-butyl) (S)-3-benzyl-2-(4-bromo-2-fluorobenzoyl)-3,4,6,7-tetrahydro-5H-imidazo[4,5-c]pyridine-5,6-dicarboxylate (I-14)

To a stirred solution of 6-benzyl 5-(tert-butyl) (S)-3-benzyl-3,4,6,7-tetrahydro-5H-imidazo[4,5-c]pyridine-5,6-dicarboxylate (I-11) (1.70 Kg, 3.80 mol) in ACN (13.6 L, 8 vol) was added triethylamine (2.11 L, 15.2 mol) followed by the addition of 4-bromo-2-fluorobenzoyl chloride (I-13) (1.08 Kg, 4.56 mol in 3.4 L ACN, 2 vol) at room temperature. After completion of addition, the resulting reaction mixture color turned brown from light yellow. The resulting reaction mixture was stirred at the same temperature for 30 min, and reaction progress was monitored by TLC. The resulting reaction mixture was quenched with ice cold water (10 L), followed by extraction with EtOAc (3×5 L) and combined organics were washed with brine solution. The organics were dried over sodium sulfate, filtered, and concentrated under reduced pressure to yield the crude product which was purified by column chromatography over silica gel (100-200M) by using eluents 20% EtOAc in hexane to obtain the desired product (I-14) (1.74 Kg, 71%). %). (m/z): [M+H]+ calcd for $C_{33}H_{31}BrFN_3O_5$ 648.14 found 648.20.

(c) 6-benzyl 5-(tert-butyl) (S)-3-benzyl-2-(6-bromo-1H-indazol-3-yl)-3,4,6,7-tetrahydro-5H-imidazo[4,5-c]pyridine-5,6-dicarboxylate (I-15)

To a stirred solution of 6-benzyl 5-(tert-butyl) (S)-3-benzyl-2-(4-bromo-2-fluorobenzoyl)-3,4,6,7-tetrahydro-5H-imidazo[4,5-c]pyridine-5,6-dicarboxylate (I-14) (1.74 Kg, 2.68 mol) in THF (26.0 L, 15 vol) was added hydrazine hydrate (0.705 L, 13.4 mol) at room temperature. The resulting reaction mixture was heated at 60° C. for 3 hours. After completion of the reaction (TLC monitoring), the resulting reaction mass was poured into ice cold water (10 L) followed by extraction of compound with EtOAc (3×10 L). The combined organics were washed with brine and dried over sodium sulfate, filtered, and evaporated under reduced pressure to yield the crude product, which was purified by column chromatography over silica gel (100-200M) by using eluents 20% EtOAc in hexane to obtain the desired product (I-15) as an off-white solid (1.12 Kg, 65%). (m/z): [M+H]+ calcd for $C_{33}H_{32}BrN_5O_4$ 642.16 found 642.21.

Preparation 4: 6-benzyl 5-(tert-butyl) (S)-3-benzyl-2-(6-(4-(benzyloxy)-2-ethylphenyl)-1H-indazol-3-yl)-3,4,6,7-tetrahydro-5H-imidazo[4,5-c]pyridine-5,6-dicarboxylate (I-16)

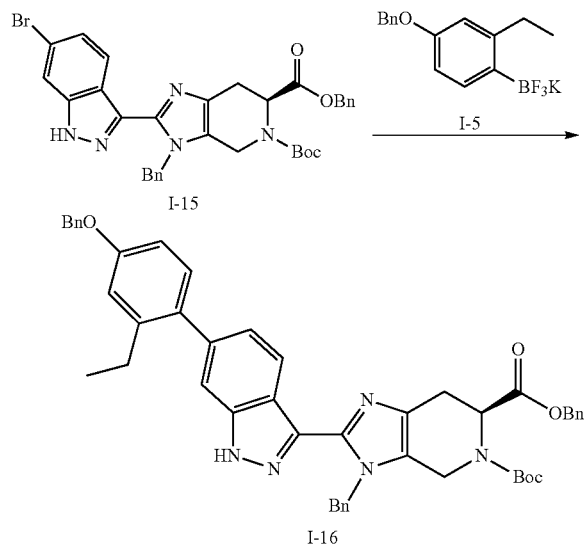

Bis(pinacolato)diboron (250 g, 984 mmol) was charged to a 5 L 3-neck single walled flask previously etched using fluoride chemistry, along with propan-2-ol (1882 mL, 2.46E+04 mmol) and the mixture was stirred until full dissolved. Dissolution was endothermic (−4° C.). In a 4 L Erlenmeyer flask, previously etched using fluoride chemistry, potassium fluoride hydrofluoride (538 g, 6891 mmol) was dissolved in water (2306 mL, 1.28E+05 mmol) to form a 3M solution. The dissolution was endothermic (−12° C.). The solution was then filtered to remove a small amount of insoluble material from the $KHF_2$. Once both solutions were fully dissolved, the contents of the Erlenmeyer flask were charged into the single walled flask portion-wise over 15 minutes. A moderate exotherm was observed (+10° C.). The solution became a thick and translucent semi-opaque gray slurry during the addition and stirring was increased to keep the contents well mixed. The mixture was stirred for 1.5 h, and then filtered through a coarse glass fritted funnel (4 L, previously etched). The filtration required 30-45 minutes to complete. The clear biphasic filtrate was discarded. The white solids were dried for 10 minutes on the filter (cracking of the cake was observed). The solids were transferred back into a cleaned 5 L 3-neck single walled flask and re-slurried with water (1330 mL, 7.38E+04 mmol). The slurry was stirred for 2 h after which time it formed a clear homogenous hydrogel. The solution was stirred for another 1 h whereupon the solids/gel were filtered out using a 4 L coarse glass funnel (previously etched). The solids were allowed to dry on the filter for 30 minutes. The solids were transferred back to a cleaned 5 L 3-neck single walled flask and reslurried in acetone (1084 mL, 1.48E+04 mmol). The white/gray slurry was stirred for 1 h and was then filtered on a 4 L coarse glass funnel (previously etched). The filtration required 20 minutes to complete, and was then dried on the funnel for another 1 h. During this time, the solids were occasionally agitated to ensure homogenous drying. A light white powder remained after drying on the filter. The solids were dried for 20 h at 55° C. under vacuum with a slow nitrogen bleed to afford a fluffy white solid (200.3 g were collected).

To a stirred solution of 6-benzyl 5-(tert-butyl) (S)-3-benzyl-2-(6-bromo-1H-indazol-3-yl)-3,4,6,7-tetrahydro-5H-imidazo[4,5-c]pyridine-5,6-dicarboxylate (I-15) (10.0 g, 16.0 mmol) in 2-methyl tetrahydrofuran (100 mL, 10 vol) was added (4-(benzyloxy)-2-ethylphenyl)trifluoro-$\lambda^4$-borane, potassium salt (I-5) (8.0 g, 20 mmol) and the fluffy white solid obtained above (0.20 g). The resulting reaction mixture was degassed with nitrogen gas for 30 minutes. To this solution, a prepared aqueous solution of cesium carbonate (20.0 g, 62.0 mmol in 60 mL water, 6 vol) was added. The resulting reaction mixture was further degassed for 15 minutes followed by addition of bis(di-tert-butyl(4-dimethylaminophenyl)phosphine)dichloropalladium(II) (0.66 g, 0.93 mmol), and the reaction mixture was evacuated under vacuum and flushed by nitrogen. The resulting reaction mixture was heated at 110° C. for 20 hours. After completion of the reaction (TLC & LCMS monitoring), the resulting reaction mixture was cooled to room temperature and filtered through a celite bed, then further washed with EtOAc (3×0.5 L). The combined organics were washed with 1N sodium hydroxide solution (3×0.5 L). The combined organics were then washed with brine and dried over sodium sulfate, filtered, and evaporated under reduced pressure to yield the crude product, which was purified by column chromatography over silica gel (100-200M) by using eluents 20% EtOAc in hexane to obtain the desired product (I-16) (as mixture of N-benzyl regioisomers) as light yellow solid (8.0 g, 66%). (m/z): [M+H]+ calcd for $C_{48}H_{47}N_5O_5$ 774.36 found 774.59.

Preparation 5: (S)-2-(6-(2-ethyl-4-hydroxyphenyl)-1H-indazol-3-yl)-4,5,6,7-tetrahydro-3H-imidazo[4,5-c]pyridine-6-carboxylic Acid, Hydrochloride (I-18)

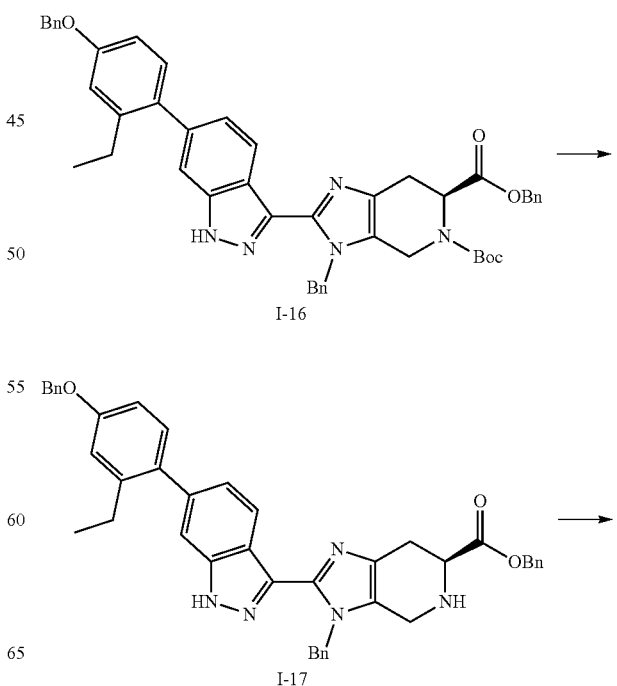

-continued

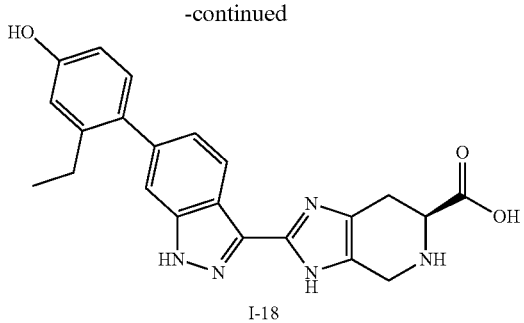

I-18

(a) benzyl (S)-3-benzyl-2-(6-(4-(benzyloxy)-2-ethyl-phenyl)-1H-indazol-3-yl)-4,5,6,7-tetrahydro-3H-imidazo[4,5-c]pyridine-6-carboxylate, Hydrochloride (I-17)

6-Benzyl 5-(tert-butyl) (S)-3-benzyl-2-(6-(4-(benzyloxy)-2-ethylphenyl)-1H-indazol-3-yl)-3,4,6,7-tetrahydro-5H-imidazo[4,5-c]pyridine-5,6-dicarboxylate (I-16) (1.0 g, 1.292 mmol) was dissolved in dioxane (8 mL) and water (1.5 mL), then hydrogenchloride solution, 4 M in dioxane (7 mL, 28.0 mmol) was added and the reaction mixture was stirred at room temperature for 3 hours (reaction progress monitored by LCMS). The reaction mixture was then frozen and lyophilized, and the crude product (I-17) was used directly in the next reaction (quantitative yield was assumed). (m/z): [M+H]+ calcd for $C_{43}H_{39}N_5O_3$ 674.31 found 674.3.

(b) (S)-2-(6-(2-ethyl-4-hydroxyphenyl)-1H-indazol-3-yl)-4,5,6,7-tetrahydro-3H-imidazo[4,5-c]pyridine-6-carboxylic Acid, Hydrochloride (I-18)

Benzyl (S)-3-benzyl-2-(6-(4-(benzyloxy)-2-ethylphenyl)-1H-indazol-3-yl)-4,5,6,7-tetrahydro-3H-imidazo[4,5-c]pyridine-6-carboxylate, hydrochloride (I-17) (0.918 g, 1.292 mmol) was dissolved in 2-Propanol (15 mL), hydrogen chloride solution, 5 M in water (0.258 mL, 1.292 mmol), and water (0.25 mL) at 50° C., then palladium, 10% wt. on carbon, 50% water (0.138 g, 0.065 mmol) was added. The reaction flask was then purged with nitrogen, a hydrogen balloon was attached, and the reaction mixture was stirred at 50° C. for 4 days with the hydrogen balloon being replenished as needed (reaction progress monitored by LCMS). All solids were then removed by filtration and the resulting solution was concentrated. The residue was dissolved in 1:1 ACN/Water, frozen, and lyophilized. The resulting powder (I-18) was used without further purification (quantitative yield was assumed). (m/z): [M+H]+ calcd for $C_{22}H_{21}N_5O_3$ 404.17 found 404.2.

Preparation 6: of (S)-2-(6-(2-ethyl-4-hydroxyphenyl)-1H-indazol-3-yl)-5-isopropyl-4,5,6,7-tetrahydro-3H-imidazo[4,5-c]pyridine-6-carboxylic acid (I-19)

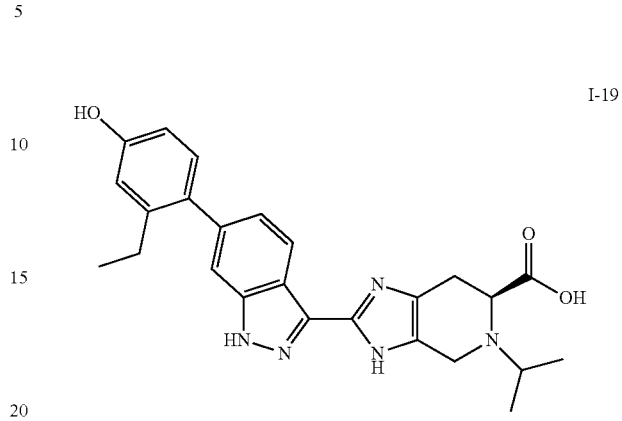

I-19

(S)-2-(6-(2-ethyl-4-hydroxyphenyl)-1H-indazol-3-yl)-4,5,6,7-tetrahydro-3H-imidazo[4,5-c]pyridine-6-carboxylic acid, HCl (I-18) (0.25 g, 0.568 mmol) was suspended in DMF (2.5 mL) and acetone (2.5 mL), then acetic acid (0.098 mL, 1.705 mmol) and sodium cyanoborohydride (0.179 g, 2.84 mmol) were added and the reaction mixture was stirred at room temperature for 24 hours (reaction progress was monitored by LCMS). The reaction mixture was concentrated, then the crude product was purified by reverse phase chromatography (5-70% ACN/Water gradient, 50 g C18aq column) to provide the TFA salt of the title compound (149 mg, 47% yield). (m/z): [M+H]+ calcd for $C_{25}H_{27}N_5O_3$ 446.21 found 446.3.

Preparation 7: (S)-2-(6-(2-ethyl-4-hydroxyphenyl)-1H-indazol-3-yl)-5-propyl-4,5,6,7-tetrahydro-3H-imidazo[4,5-c]pyridine-6-carboxylic Acid (I-20)

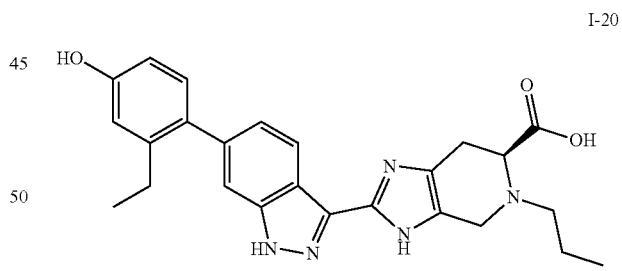

I-20

(S)-2-(6-(2-ethyl-4-hydroxyphenyl)-1H-indazol-3-yl)-4,5,6,7-tetrahydro-3H-imidazo[4,5-c]pyridine-6-carboxylic acid, HCl (I-18) (0.160 g, 0.364 mmol) and propionaldehyde (0.039 mL, 0.546 mmol) were dissolved in methanol (3.0 mL), then sodium cyanoborohydride (0.069 g, 1.091 mmol) was added and the reaction mixture was stirred at room temperature for 24 hours (reaction progress was monitored by LCMS). The reaction mixture was concentrated and the crude product was purified by reverse phase chromatography (5-70% ACN/Water gradient, 50 g C18 column) to provide the TFA salt of the title compound (78 mg, 38% yield). (m/z): [M+H]+ calcd for $C_{25}H_{27}N_5O_3$ 446.21 found 446.3.

Preparation 8: (S)-2-(6-(2-ethyl-4-hydroxyphenyl)-1H-indazol-3-yl)-5-methyl-4,5,6,7-tetrahydro-3H-imidazo[4,5-c]pyridine-6-carboxylic Acid (I-21)

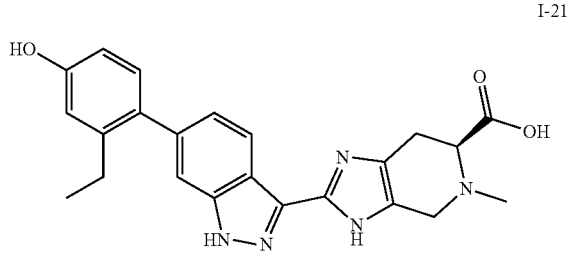 [SMILES: CCc1cc(O)ccc1-c1ccc2c(-c3nc4c([nH]3)CN(C)[C@H](C(=O)O)C4)n[nH]c2c1]

I-21

(S)-2-(6-(2-ethyl-4-hydroxyphenyl)-1H-indazol-3-yl)-4,5,6,7-tetrahydro-3H-imidazo[4,5-c]pyridine-6-carboxylic acid, HCl (I-18) (0.160 g, 0.364 mmol) and formaldehyde solution, 37 wt % in water (0.032 mL, 0.436 mmol) were dissolved in methanol (3.0 mL), then sodium cyanoborohydride (0.069 g, 1.091 mmol) was added and the reaction mixture was stirred at room temperature for 4 hours (reaction progress was monitored by LCMS). Sodium borohydride (14 mg, 0.364 mmol) was added to quench ant excess formaldehyde, then the reaction mixture was concentrated. The crude product was purified by reverse phase chromatography (5-70% ACN/Water gradient, 50 g C18 column) to provide the TFA salt of the title compound (110 mg, 57% yield). (m/z): [M+H]+ calcd for $C_{23}H_{23}N_5O_3$ 418.18 found 418.2.

Preparation 9: (R)-2-(3-methylpiperazin-1-yl)ethan-1-ol, Dihydrochloride (I-24)

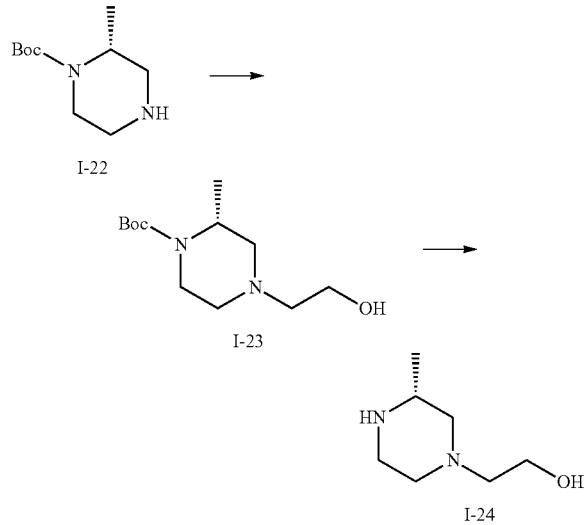

(a) tert-butyl (R)-4-(2-hydroxyethyl)-2-methylpiperazine-1-carboxylate (I-23)

(R)-1-boc-2-methyl-piperazine (0.2 g, 0.999 mmol), DIPEA (0.698 mL, 3.99 mmol), and 2-bromoethanol (0.085 mL, 1.198 mmol) were dissolved in DMF (5 mL) and the reaction mixture was stirred at 60° C. for 16 hours (reaction progress was monitored by LCMS). The reaction mixture was concentrated, then 10 mL of diethyl ether was added to the residue. The solution was sonicated until the residue gel had disappeared and a solid had formed. The ether solution was then decanted away from the solid. The solid was then used directly in the next reaction (quantitative yield was assumed). (m/z): [M+H]+ calcd for $C_{12}H_{24}N_2O_3$ 245.18 found 245.4.

(b) (R)-2-(3-methylpiperazin-1-yl)ethan-1-ol, Dihydrochloride (I-24)

Tert-butyl (R)-4-(2-hydroxyethyl)-2-methylpiperazine-1-carboxylate (0.244 g, 0.999 mmol) was dissolved in Dioxane (3.0 mL) and Water (0.5 mL), then hydrogen chloride solution, 4 M in Dioxane (2.0 mL, 65.8 mmol) was added and the reaction mixture was stirred at room temperature for 3 hours (reaction progress was monitored by LCMS). The reaction mixture was frozen and lyophilized, and the resulting product was used without purification (quantitative yield was assumed). (m/z): [M+H]+ calcd for $C_7H_{16}N_2O$ 145.13 found 145.4.

Example 1: (S)-(2-(6-(2-ethyl-4-hydroxyphenyl)-1H-indazol-3-yl)-5-propyl-4,5,6,7-tetrahydro-3H-imidazo[4,5-c]pyridin-6-yl)(4-(2-hydroxyethyl)piperazin-1-yl)methanone

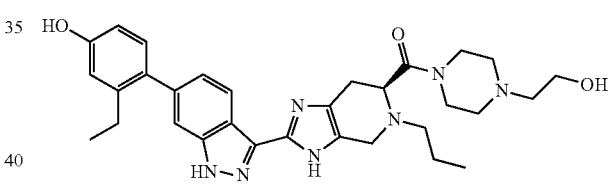

1

(S)-2-(6-(2-ethyl-4-hydroxyphenyl)-1H-indazol-3-yl)-5-propyl-4,5,6,7-tetrahydro-3H-imidazo[4,5-c]pyridine-6-carboxylic acid, TFA (I-20) (40 mg, 0.071 mmol), n-(2-hydroxyethyl)piperazine (0.018 mL, 0.143 mmol), and DIPEA (0.025 mL, 0.143 mmol) were dissolved in DMF (1.5 mL), then HATU (40.8 mg, 0.107 mmol) was added and the reaction mixture was stirred at room temperature for 3 hours (reaction progress was monitored by LCMS). Hydrazine (0.011 mL, 0.357 mmol) was added to cleave undesired byproducts, then the solution was stirred at room temperature for 10 minutes. The reaction mixture was then concentrated and the crude product was purified by preparative HPLC (5-70% ACN/Water gradient, C18 column) to provide the TFA salt of the title compound (31 mg, 56% yield). (m/z): [M+H]+ calcd for $C_{31}H_{39}N_7O_3$ 558.31 found 558.3. $^1$H NMR (400 MHz, DMSO-d6) δ 13.10 (s, 1H), 12.27 (d, J=48.92 Hz, 1H), 9.40 (s, 1H), 8.28 (t, J=8.10 Hz, 1H), 7.30 (s, 1H), 7.04 (m, 2H), 6.71 (d, J=2.46 Hz, 1H), 6.64 (dd, J=2.50, 8.23 Hz, 1H), 4.44 (t, J=5.31 Hz, 1H), 4.11 (q, J=5.26, 2H), 3.96 (m, 1H), 3.86-3.52 (m, 6H), 3.49 (q, J=6.01 Hz, 2H), 2.95 (m, 2H), 2.48 (q, J=7.48 Hz, 2H), 2.42-2.21 (m, 4H), 2.37 (t, J=6.20 Hz, 2H), 1.42 (m, 2H), 1.00 (t, J=7.52 Hz, 3H), 0.81 (m, 3H).

Example 2: ((S)-2-(6-(2-ethyl-4-hydroxyphenyl)-1H-indazol-3-yl)-5-propyl-4,5,6,7-tetrahydro-3H-imidazo[4,5-c]pyridin-6-yl)((1S,4S)-5-methyl-2,5-diazabicyclo[2.2.1]heptan-2-yl)methanone

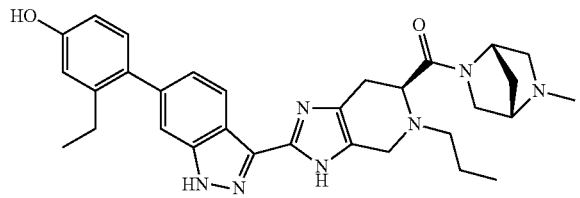

2

(S)-2-(6-(2-ethyl-4-hydroxyphenyl)-1H-indazol-3-yl)-5-propyl-4,5,6,7-tetrahydro-3H-imidazo[4,5-c]pyridine-6-carboxylic acid, TFA (I-20) (40 mg, 0.071 mmol), (1S,4S)-5-Methyl-2,5-diazabicyclo[2.2.1]heptane dihydrobromide (29.4 mg, 0.107 mmol), and DIPEA (0.062 mL, 0.357 mmol) were dissolved in DMF (1.5 mL), then HATU (40.8 mg, 0.107 mmol) was added and the reaction mixture was stirred at room temperature for 3 hours (reaction progress was monitored by LCMS). Hydrazine (0.011 mL, 0.357 mmol) was added to cleave undesired byproducts, then the solution was stirred at room temperature for 10 minutes. The reaction mixture was then concentrated and the crude product was purified by preparative HPLC (5-70% ACN/Water gradient, C18 column) to provide the TFA salt of the title compound (32 mg, 59% yield). (m/z): [M+H]+ calcd for $C_{31}H_{37}N_7O_2$ 540.30 found 540.3.

Example 3: ((S)-2,4-dimethylpiperazin-1-yl)((S)-2-(6-(2-ethyl-4-hydroxyphenyl)-1H-indazol-3-yl)-5-methyl-4,5,6,7-tetrahydro-3H-imidazo[4,5-c]pyridin-6-yl)methanone 3

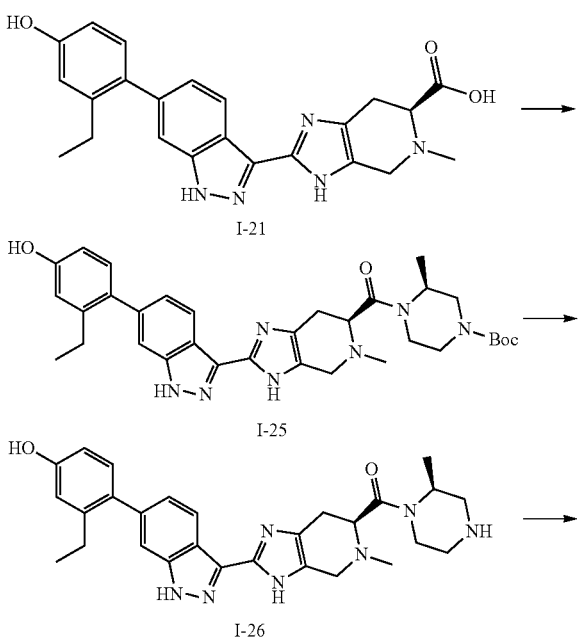

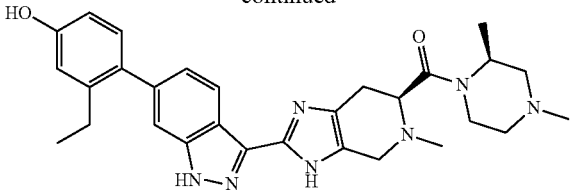

3

(a) tert-butyl (S)-4-((S)-2-(6-(2-ethyl-4-hydroxyphenyl)-1H-indazol-3-yl)-5-methyl-4,5,6,7-tetrahydro-3H-imidazo[4,5-c]pyridine-6-carbonyl)-3-methyl-piperazine-1-carboxylate (I-25)

(S)-2-(6-(2-ethyl-4-hydroxyphenyl)-1H-indazol-3-yl)-5-methyl-4,5,6,7-tetrahydro-3H-imidazo[4,5-c]pyridine-6-carboxylic acid, TFA (I-21) (55 mg, 0.103 mmol), (s)-4-n-boc-2-methylpiperazine (41.5 mg, 0.207 mmol), and DIPEA (0.036 mL, 0.207 mmol) were dissolved in DMF (1.5 mL), then HATU (59.0 mg, 0.155 mmol) was added and the reaction mixture was stirred at room temperature for 16 hours (reaction progress was monitored by LCMS). Hydrazine (0.016 mL, 0.517 mmol) was added to cleave undesired byproducts, then the reaction mixture was stirred at room temperature for 10 minutes. The reaction mixture was then concentrated and the crude product was purified by reverse phase chromatography (5-70% ACN/Water gradient, 50 g C18 column) to provide the TFA salt of the title compound (54 mg, 72% yield). (m/z): [M+H]+ calcd for $C_{33}H_{41}N_7O_4$ 600.33 found 600.3.

(b) ((S)-2-(6-(2-ethyl-4-hydroxyphenyl)-1H-indazol-3-yl)-5-methyl-4,5,6,7-tetrahydro-3H-imidazo[4,5-c]pyridin-6-yl)((S)-2-methylpiperazin-1-yl)methanone (I-26)

Tert-butyl (S)-4-((S)-2-(6-(2-ethyl-4-hydroxyphenyl)-1H-indazol-3-yl)-5-methyl-4,5,6,7-tetrahydro-3H-imidazo[4,5-c]pyridine-6-carbonyl)-3-methylpiperazine-1-carboxylate, TFA (I-25) (0.126 g, 0.177 mmol) was dissolved in dioxane (1.5 mL) and water (0.3 mL), then hydrogen chloride solution, 4 M in dioxane (1.5 mL, 6.00 mmol) was added and the reaction mixture was stirred at room temperature for 2 hours (reaction progress was monitored by LCMS). The reaction mixture was frozen and lyophilized and the resulting powder was used directly in the next reaction (quantitative yield was assumed). (m/z): [M+H]+ calcd for $C_{28}H_{33}N_7O_2$ 500.27 found 500.3.

(c) ((S)-2,4-dimethylpiperazin-1-yl)((S)-2-(6-(2-ethyl-4-hydroxyphenyl)-1H-indazol-3-yl)-5-methyl-4,5,6,7-tetrahydro-3H-imidazo[4,5-c]pyridin-6-yl)methanone ((S)-2-(6-(2-ethyl-4-hydroxyphenyl)-1H-indazol-3-yl)-5-methyl-4,5,6,7-tetrahydro-3H-imidazo[4,5-c]pyridin-6-yl)((S)-2-methylpiperazin-1-yl)methanone, dihydrochloride (0.101 g, 0.176 mmol) and formaldehyde solution, 37 wt % in water (0.016 mL, 0.212 mmol) were dissolved in Methanol (3.0 mL), then sodium cyanoborohydride (0.055 g, 0.882 mmol) was added and the reaction mixture was stirred at room temperature for 16 hours (reaction progress was monitored by LCMS). Sodium borohydride (7 mg, 0.176 mmol) was added to quench any remaining formaldehyde. The reaction mixture was concentrated, then the crude product was purified by preparative HPLC (5-60% ACN/Water gradient, C18 column) to provide the TFA salt of the title compound (28 mg, 21% yield). (m/z): [M+H]+ calcd for $C_{29}H_{35}N_7O_2$ 514.29 found 514.3.

Example 4: (S)-(2-(6-(2-ethyl-4-hydroxyphenyl)-1H-indazol-3-yl)-5-isopropyl-4,5,6,7-tetrahydro-3H-imidazo[4,5-c]pyridin-6-yl)(4-methyl-1,4-diazepan-1-yl)methanone

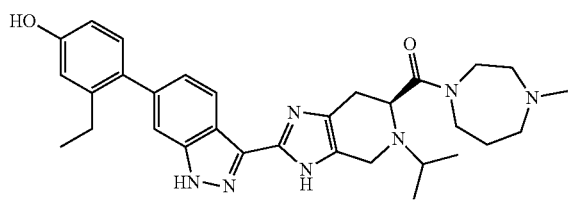

(S)-2-(6-(2-ethyl-4-hydroxyphenyl)-1H-indazol-3-yl)-5-isopropyl-4,5,6,7-tetrahydro-3H-imidazo[4,5-c]pyridine-6-carboxylic acid, TFA (I-19) (50 mg, 0.089 mmol), 1-methylhomopiperazine (0.022 mL, 0.179 mmol), and DIPEA (0.031 mL, 0.179 mmol) were dissolved in DMF (1.5 mL), then HATU (51.0 mg, 0.134 mmol) was added and the reaction mixture was stirred at room temperature for 3 hours (reaction progress was monitored by LCMS). Hydrazine (0.014 mL, 0.447 mmol) was added to cleave undesired byproducts, and the solution was stirred at room temperature for 10 minutes. The reaction mixture was then concentrated and the crude product was purified by preparative HPLC (2-70% ACN/Water gradient, C18 column) to provide the TFA salt of the title compound (29 mg, 42% yield). (m/z): [M+H]+ calcd for $C_{31}H_{39}N_7O_2$ 542.32 found 542.3. $^1H$ NMR (400 MHz, DMSO-d6) δ 13.08 (s, 1H), 12.21 (d, J=29.9 Hz, 1H), 9.40 (s, 1H), 8.27 (d, J=8.33 Hz, 1H), 7.30 (s, 1H), 7.04 (t, J=8.05, 2H), 6.71 (d, J=2.53 Hz, 1H), 6.64 (dd, J=2.54, 8.23 Hz, 1H), 4.11 (m, 3H), 3.91-3.52 (m, 6H), 2.97 (m, 1H), 2.91-2.53 (m, 4H), 2.49 (q, J=7.46, 2H), 2.23 (d, J=13.9 Hz, 3H), 1.76 (m, 2H), 1.0 (m, 9H).

Example 5: ((S)-2-(6-(2-ethyl-4-hydroxyphenyl)-1H-indazol-3-yl)-5-methyl-4,5,6,7-tetrahydro-3H-imidazo[4,5-c]pyridin-6-yl)((R)-4-(2-hydroxyethyl)-2-methylpiperazin-1-yl)methanone

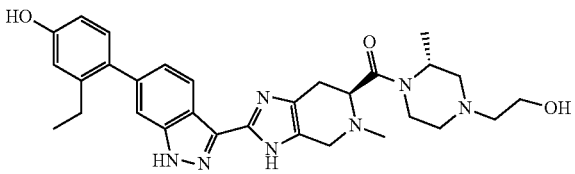

(S)-2-(6-(2-ethyl-4-hydroxyphenyl)-1H-indazol-3-yl)-5-methyl-4,5,6,7-tetrahydro-3H-imidazo[4,5-c]pyridine-6-carboxylic acid, TFA (I-21) (55 mg, 0.103 mmol), (R)-2-(3-methylpiperazin-1-yl)ethan-1-ol, dihydrochloride (I-24) (33.7 mg, 0.155 mmol), and DIPEA (0.090 mL, 0.517 mmol) were dissolved in DMF (1.5 mL), then HATU (59.0 mg, 0.155 mmol) was added and the reaction mixture was stirred at room temperature for 16 hours (reaction progress was monitored by LCMS). Hydrazine (0.016 mL, 0.517 mmol) was added to cleave undesired byproducts, then the reaction mixture was stirred at room temperature for 10 minutes. The reaction mixture was then concentrated, and the crude product was purified by preparative HPLC (5-70% ACN/Water gradient, C18 column) to provide the TFA salt of the title compound (22 mg, 28% yield). (m/z): [M+H]+ calcd for $C_{30}H_{37}N_7O_3$ 544.30 found 544.3.

Example 6: ((S)-3-(dimethylamino)pyrrolidin-1-yl)((S)-2-(6-(2-ethyl-4-hydroxyphenyl)-1H-indazol-3-yl)-5-isopropyl-4,5,6,7-tetrahydro-3H-imidazo[4,5-c]pyridin-6-yl)methan One

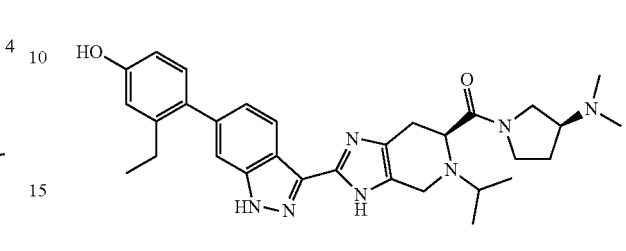

(S)-2-(6-(2-ethyl-4-hydroxyphenyl)-1H-indazol-3-yl)-5-isopropyl-4,5,6,7-tetrahydro-3H-imidazo[4,5-c]pyridine-6-carboxylic acid, TFA (I-19) (50 mg, 0.089 mmol), (S)-(−)-3-(dimethylamino)pyrrolidine (0.023 mL, 0.179 mmol), and DIPEA (0.031 mL, 0.179 mmol) were dissolved in DMF (1.5 ml), then HATU (51.0 mg, 0.134 mmol) was added and the reaction mixture was stirred at room temperature for 3 hours (reaction progress was monitored by LCMS). Hydrazine (0.014 mL, 0.447 mmol) was added to cleave undesired byproducts, and the solution was stirred at room temperature for 10 minutes. The reaction mixture was then concentrated and the crude product was purified by preparative HPLC (5-70% ACN/Water gradient, C18 column) to provide the TFA salt of the title compound (37 mg, 53% yield). (m/z): [M+H]+ calcd for $C_{31}H_{39}N_7O_2$ 542.32 found 542.3.

Example 7: (S)-(3-(dimethylamino)azetidin-1-yl)(2-(6-(2-ethyl-4-hydroxyphenyl)-1H-indazol-3-yl)-5-isopropyl-4,5,6,7-tetrahydro-3H-imidazo[4,5-c]pyridin-6-yl)methan One

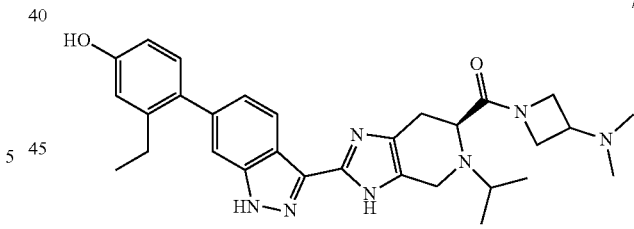

(S)-2-(6-(2-ethyl-4-hydroxyphenyl)-1H-indazol-3-yl)-5-isopropyl-4,5,6,7-tetrahydro-3H-imidazo[4,5-c]pyridine-6-carboxylic acid, TFA (I-19) (50 mg, 0.089 mmol), 3-(Dimethylamino)azetidine dihydrochloride (23.20 mg, 0.134 mmol), and DIPEA (0.078 mL, 0.447 mmol) were dissolved in DMF (1.5 mL), then HATU (51.0 mg, 0.134 mmol) was added and the reaction mixture was stirred at room temperature for 3 hours (reaction progress was monitored by LCMS). Hydrazine (0.014 mL, 0.447 mmol) was added to cleave undesired byproducts, and the solution was stirred at room temperature for 10 minutes. The reaction mixture was then concentrated and the crude product was purified by preparative HPLC (5-70% ACN/Water gradient, C18 column) to provide the TFA salt of the title compound (25 mg, 37% yield). (m/z): [M+H]+ calcd for $C_{30}H_{37}N_7O_2$ 528.30 found 528.3. $^1H$ NMR (400 MHz, DMSO-d6) δ 13.09 (s, 1H), 9.40 (s, 1H), 8.27 (d, J=8.31, 1H), 7.30 (s, 1H), 7.04 (m, 2H), 6.71 (d, J=2.54, 1H), 6.64 (dd, J=2.53, 8.26 Hz, 1H), 4.26

(m, 1H), 4.06 (m, 2H), 3.82 (m, 2H), 3.64 (m, 2H), 3.03 (m, 2H), 2.74 (m, 2H), 2.47 (q, J=7.56, 2H), 2.07 (d, J=3.69, 6H), 1.07 (m, 6H), 1.00 (t, J=7.50, 3H).

Preparation 10: 6-benzyl 5-(tert-butyl) (S)-1-benzyl-2-(6-(4-(benzyloxy)-2-ethyl-5-fluorophenyl)-1H-indazol-3-yl)-1,4,6,7-tetrahydro-5H-imidazo[4,5-c]pyridine-5,6-dicarboxylate

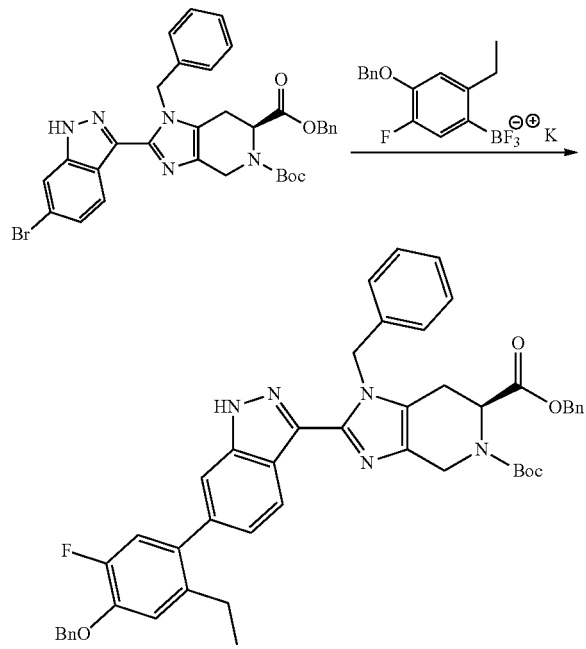

To a stirred solution of 6-benzyl 5-(tert-butyl) (S)-1-benzyl-2-(6-bromo-1H-indazol-3-yl)-1,4,6,7-tetrahydro-5H-imidazo[4,5-c]pyridine-5,6-dicarboxylate (1.12 Kg, 1.74 mol) in 2-methyltetrahydrofuran (11.2 L, 10 Vol.) was added ((4-(benzyloxy)-2-ethyl-5-fluorophenyl)trifluoroborane, potassium salt) (0.702 Kg, 2.1 mol) and the fluffy white solid isolated in Preparation 4 (0.223 Kg, 1.04 mol). The resulting reaction mixture was degassed with nitrogen gas for next 30 min through a dropper inlet. To this solution, a prepared aqueous solution of $Cs_2CO_3$ (2.27 Kg, 6.96 mol in 7.30 L $H_2O$, 6 vol) was added. The resulting reaction mixture was further degassed over next 15 min. Pd(amphos) (0.74 Kg, 1.04 mol) was added into the resulting reaction mixture and the reaction mixture was evacuated under vacuum and flushed by nitrogen. The resulting reaction mixture was heated to 90° C. for 20 hours. After completion of the reaction, the resulting reaction mixture was cooled to room temperature and filtered through celite bed, and washed with ethyl acetate (3×7.5 L). The combined organics were washed with 1N NaOH solution (3×3 L). The combined organics were washed with brine and dried over $Na_2SO_4$, filtered and evaporated under reduced pressure to get the crude which was purified with column chromatography over silica gel (100-200M) by using eluents 20% ethyl acetate in hexane to obtain the title product as a mixture of region-isomers as an off-white solid (1.10 Kg, 80%). (m/z): $[M+H]^+$ calculated for $C_{48}H_{46}FN_5O_5$ 792.92 found 792.34.

Preparation 11: Benzyl (S)-1-benzyl-2-(6-(4-(benzyloxy)-2-ethyl-5-fluorophenyl)-1H-indazol-3-yl)-4,5,6,7-tetrahydro-1H-imidazo[4,5-c]pyridine-6-carboxylate, 2Benzenesulfonic Acid

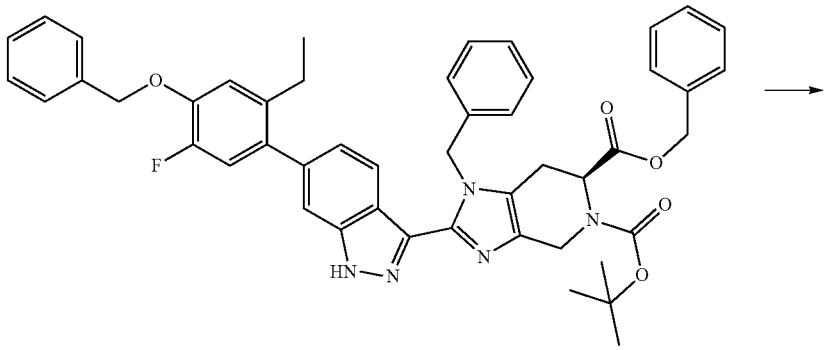

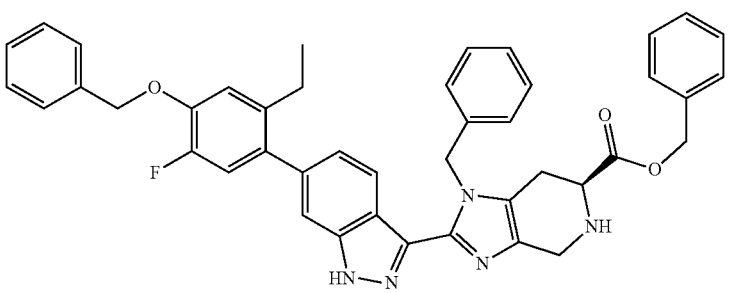

To a solution of 6-benzyl 5-(tert-butyl) (S)-1-benzyl-2-(6-(4-(benzyloxy)-2-ethyl-5-fluorophenyl)-1H-indazol-3-yl)-1,4,6,7-tetrahydro-5H-imidazo[4,5-c]pyridine-5,6-dicarboxylate (1,005 g, 1269 mmol) in 2-methyltetrahydrofuran (10,050 mL) and isopropyl acetate (4,321.5 mL) under nitrogen was added benzenesulfonic acid (703 g, 4,442 mmol). The resulting reaction mixture was stirred at 50° C. over 15 hours. To the completed reaction was added isopropyl acetate (5,728.5 mL). The slurry was cooled to 20° C. and held over 1 hour. The thickened slurry was then filtered under nitrogen pressure. The cake was then rinsed with isopropyl acetate (5,000 mL) and dried under nitrogen pressure at 25° C. over 2 hours followed by further drying at 60° C. over 16 hours under high vacuum with nitrogen bleed to afford the titled compound as an off white free flowing solid (1,210 g, 95% yield). (m/z): [M+H]$^+$ calculated for $C_{43}H_{38}FN_5O_3$ 692.81 found 692.88.

Preparation 12: Benzyl (S)-1-benzyl-2-(6-(4-(benzyloxy)-2-ethyl-5-fluorophenyl)-1H-indazol-3-yl)-5-isopropyl-4,5,6,7-tetrahydro-1H-imidazo[4,5-c]pyridine-6-carboxylate rahydro-1H-imidazo[4,5-c]pyridine-6-carboxylate, 2Benzenesulfonic acid (1.20 Kg, 1,190 mmol) and acetic acid (26 mL, 446 mmol). The suspension was allowed to stir at 25° C. over 30 minutes to afford a heterogeneous off-white to yellow heterogeneous mixture. To the reaction mixture was added sodium triacetoxyborohydride (492 g, 2,321 mmol) and stirred at 25° C. over 1 hour. The reaction mixture was filtered through celite and the cake was washed with 2-methyltetrahydrofuran (500 mL). The filtrate was diluted with 2-methyltetrahydrofuran (8.0 L) and solvent swapped by distillation of acetone. To wash the solution was added saturated sodium bicarbonate (3,025 mL) and the mixture was stirred for 1 hour, stirring was stopped, layers were separated over 15 minutes, aqueous layer (pH=7.5) was discarded and the wash was repeated this time allowing 2 hours stir time prior to layer separation. The organic layer was distilled down to 2.0 L, isopropyl acetate (8.0 L) was added and solvent swapped by distillation of 2-methyltetrahydrofuran to afford a slurry. The slurry stirred at 20° C. over 1 hour then filtered under nitrogen pressure to afford the

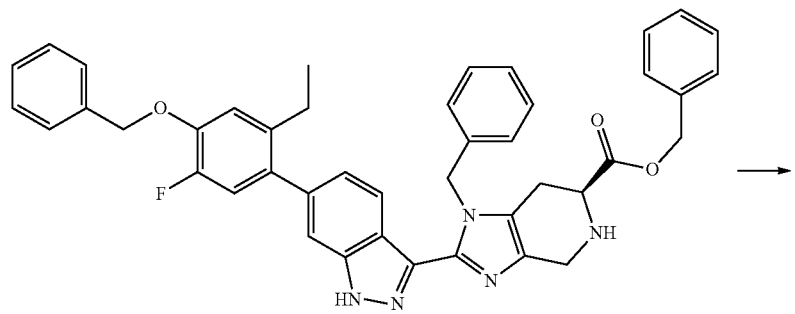

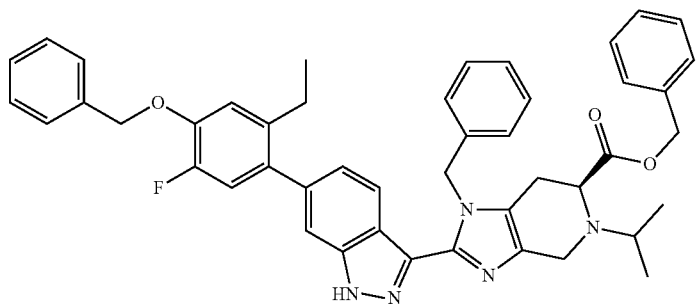

To a suspension of Molecular Sieves (1.21 Kg) in acetone (12.0 L) was added benzyl (S)-1-benzyl-2-(6-(4-(benzyloxy)-2-ethyl-5-fluorophenyl)-1H-indazol-3-yl)-4,5,6,7-tettitle compound as an off white solid (795 g, 91% yield). (m/z): [M+H]$^+$ calculated for $C_{46}H_{44}FN_5O_3$ 734.89 found 734.96.

Preparation 13: (S)-2-(6-(2-ethyl-5-fluoro-4-hydroxyphenyl)-1H-indazol-3-yl)-5-isopropyl-4,5,6,7-tetrahydro-3H-imidazo[4,5-c]pyridine-6-carboxylic Acid, 2HCl Example 8: (S)-(3-(dimethylamino)azetidin-1-yl)(2-(6-(2-ethyl-5-fluoro-4-hydroxyphenyl)-1H-indazol-3-yl)-5-isopropyl-4,5,6,7-tetrahydro-3H-imidazo[4,5-c]pyridin-6-yl)methanone

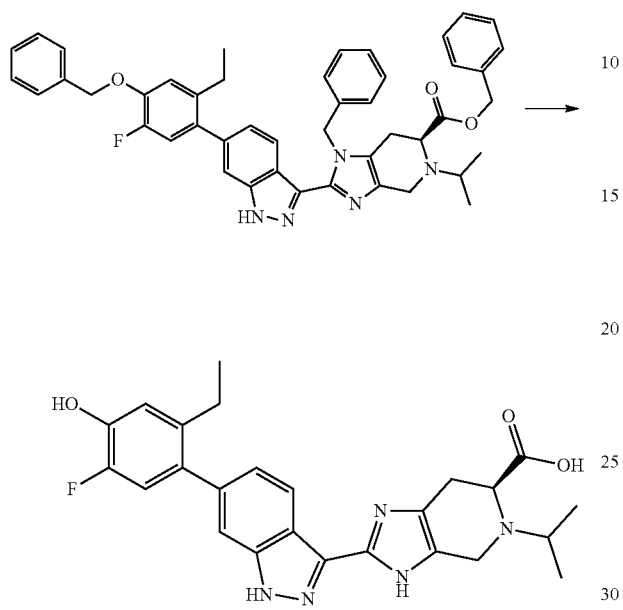

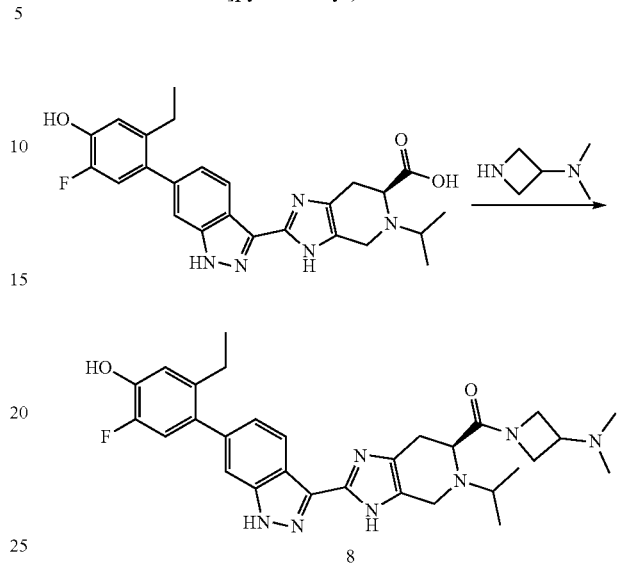

To a degassed, stirred, homogeneous solution of benzyl (S)-1-benzyl-2-(6-(4-(benzyloxy)-2-ethyl-5-fluorophenyl)-1H-indazol-3-yl)-5-isopropyl-4,5,6,7-tetrahydro-1H-imidazo[4,5-c]pyridine-6-carboxylate (760 g, 1,036 mmol), propan-2-ol (3,800 mL) and 1M hydrogen chloride(aq) (2589 mL, 2,589 mmol) at 50° C. was added 10 wt % Pd/C, 50 wt % $H_2O$ (76 g, 35.7 mmol) immediately followed by the bubbling of hydrogen gas through the reaction mixture over 4 hours. Reaction mixture filtered through celite (200 gram) pad. To the clear dark yellow filtrate was added SiliaMetS Thiol (76 g, as a white solid) and stirred at 50° C. over 1 hour to scavenge the remainder of the Palladium. The SiliaMetS Thiol was filtered off through a 0.2 micron filter to afford a light yellow colored homogeneous filtrate, SiliaMetS Thiol is was then bright orange. To the filtrate was added isopropyl acetate (7,600 mL) and it was concentrated on rotovap to approximately 3.0 liters. To the concentrated solution, as a hazy suspension, was added isopropyl acetate (7,600 mL) followed by concentration to approximately 3.0 liters. To the concentrate, then as a thick slurry, was added isopropyl acetate (7,600 mL) at which point the slurry was free flowing and filterable. The slurry was filtered and the cake rinsed with isopropyl acetate (3,000 mL), dried under high vacuum over 1 hour then further dried under high vacuum with nitrogen bleed at 50° C. over 18 hours to afford the titled compound (472 g, 81% yield). (m/z): $[M+H]^+$ calculated for $C_{25}H_{26}FN_5O_3$ 464.51 found 464.58.

To a stirred solution of (S)-2-(6-(2-ethyl-5-fluoro-4-hydroxyphenyl)-1H-indazol-3-yl)-5-isopropyl-4,5,6,7-tetrahydro-3H-imidazo[4,5-c]pyridine-6-carboxylic acid, 2HCl (470 g, 876 mmol) and N,N-dimethylazetidin-3-amine, 2HCl (197 g, 1,139 mmol) in N,N-dimethylacetamide (2,436 mL) cooled to −20° C., was added DIPEA (413 mL, 2,366 mmol) over not less than 15 minutes (the exothermic addition caused batch temperature to raise to −9.1° C.). The batch was cooled back down to −15° C. and HCTU (453 g, 1095 mmol) was added. The mixture was warmed to 20° C. over 1 hour and held for an additional hour. Into the completed reaction mixture was added isopropyl acetate (5.0 L) and 1M HCl (2.0 L) and the mixture was stirred over 15 minutes, the layers were separated to extract impurities into the isopropyl acetate layer. The aqueous layer which contained the product was extracted three additional times with isopropyl acetate (5.0 L each). After the 4$^{th}$ extraction the aqueous layer was added to 2-methyltetrahydrofuran followed by saturated sodium bicarbonate solution (~2.2 L, to adjust pH=8) stirred 15 minutes, the layers were separated, and the aqueous layer discarded. The organic layer was solvent swapped to acetonitrile and stirred at a final volume of 2.35 L at which time the product precipitated out of solution as amorphous filterable solids. The slurry was then filtered under nitrogen pressure to afford 345 grams of crude product. The crude product (345 g) was dissolved in methanol (1.035 L) with stirring at 55° C. was held over 15 hours to crystallize the product out of solution. The slurry was cooled to 10° C. and held at that temperature with stirring over 2 hours. The thickened slurry was filtered under nitrogen pressure over 2 hours at 20° C. followed by further drying under high vacuum with nitrogen bleed at 65° C. over 18 hours to afford the title compound as an off white to white free flowing solid (253 g, 53% yield). (m/z): $[M+H]^+$ calculated for $C_{30}H_{36}FN_7O_2$ 546.66 found 546.73.

Preparation 14: (S)-5-ethyl-2-(6-(2-ethyl-4-hydroxy-phenyl)-1H-indazol-3-yl)-4,5,6,7-tetrahydro-3H-imidazo[4,5-c]pyridine-6-carboxylic Acid

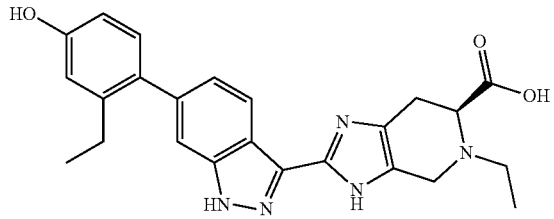 [SMILES: CCc1cc(O)ccc1-c1ccc2c(-c3nc4c([nH]3)CN(CC)[C@H](C(=O)O)C4)n[nH]c2c1]

(S)-2-(6-(2-ethyl-4-hydroxyphenyl)-1H-indazol-3-yl)-4,5,6,7-tetrahydro-3H-imidazo[4,5-c]pyridine-6-carboxylic acid, HCl (0.100 g, 0.227 mmol) (I-18) and acetaldehyde (0.019 mL, 0.341 mmol) were dissolved in methanol (3.0 mL), then sodium cyanoborohydride (0.057 g, 0.909 mmol) was added and the reaction mixture was stirred at room temperature for 16 hours (reaction progress was monitored by LCMS). Sodium borohydride (9 mg, 0.227 mmol) was added to quench any remaining acetaldehyde, then the reaction mixture was concentrated. The crude product was then purified by reverse phase chromatography (5-70% ACN/Water gradient, 40 g C18 column) to provide the TFA salt of the title compound (62 mg, 50% yield). (m/z): [M+H]+ calcd for $C_{24}H_{25}N_5O_3$ 432.20 found 432.1.

Example 9: (S)-(3-(dimethylamino)azetidin-1-yl)(5-ethyl-2-(6-(2-ethyl-4-hydroxyphenyl)-1H-indazol-3-yl)-4,5,6,7-tetrahydro-3H-imidazo[4,5-c]pyridin-6-yl)methanone

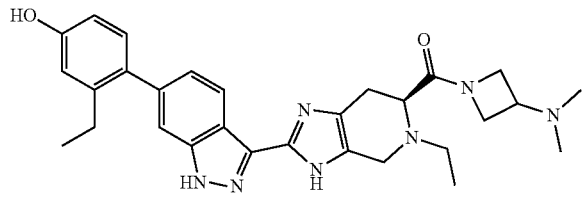

(S)-5-ethyl-2-(6-(2-ethyl-4-hydroxyphenyl)-1H-indazol-3-yl)-4,5,6,7-tetrahydro-3H-imidazo[4,5-c]pyridine-6-carboxylic acid, TFA (30 mg, 0.055 mmol), 3-(dimethylamino)azetidine dihydrochloride (14.28 mg, 0.082 mmol), and DIPEA (0.048 mL, 0.275 mmol) were dissolved in DMF (1.50 mL), then HATU (31.4 mg, 0.082 mmol) was added and the reaction mixture was stirred at room temperature for 1 hour (reaction progress was monitored by LCMS). Hydrazine (5.18 µl, 0.165 mmol) was added to cleave undesired byproducts, then the solution was stirred at room temperature for 10 minutes. The reaction mixture was then concentrated and the crude product was purified by preparative HPLC (5-60% ACN/Water gradient, C18 column) to provide the TFA salt of the title compound (25 mg, 63% yield). (m/z): [M+H]+ calcd for $C_{29}H_{35}N_7O_2$ 514.29 found 514.2.

Example 10: (S)-(3-(dimethylamino)-3-methylazetidin-1-yl)(5-ethyl-2-(6-(2-ethyl-4-hydroxyphenyl)-1H-indazol-3-yl)-4,5,6,7-tetrahydro-3H-imidazo[4,5-c]pyridin-6-yl)methan One

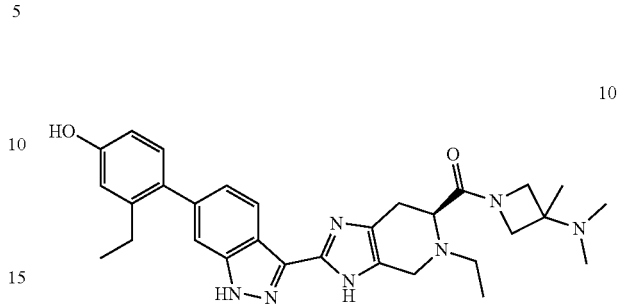

(S)-5-ethyl-2-(6-(2-ethyl-4-hydroxyphenyl)-1H-indazol-3-yl)-4,5,6,7-tetrahydro-3H-imidazo[4,5-c]pyridine-6-carboxylic acid, TFA (30 mg, 0.055 mmol), N,N,3-trimethylazetidin-3-amine hydrochloride (12.43 mg, 0.082 mmol), and DIPEA (0.048 mL, 0.275 mmol) were dissolved in DMF (1.50 mL), then HATU (31.4 mg, 0.082 mmol) was added and the reaction mixture was stirred at room temperature for 1 hour (reaction progress was monitored by LCMS). Hydrazine (5.18 µl, 0.165 mmol) was added to cleave undesired byproducts, then the solution was stirred at room temperature for 10 minutes. The reaction mixture was then concentrated and the crude product was purified by preparative HPLC (5-60% ACN/Water gradient, C18 column) to provide the TFA salt of the title compound (25 mg, 62% yield). (m/z): [M+H]+ calcd for $C_{30}H_{37}N_7O_2$ 528.30 found 528.2.

Example 11: (S)-(3-(dimethylamino)-3-methylazetidin-1-yl)(2-(6-(2-ethyl-4-hydroxyphenyl)-1H-indazol-3-yl)-5-isopropyl-4,5,6,7-tetrahydro-3H-imidazo[4,5-c]pyridin-6-yl)methan One

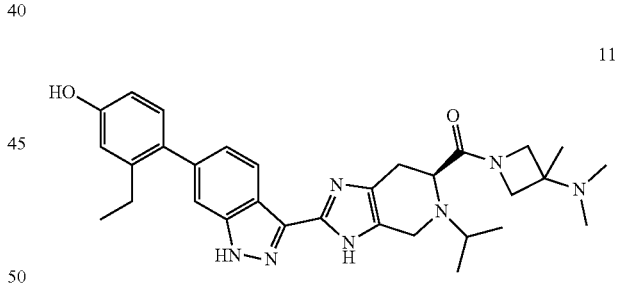

(S)-2-(6-(2-ethyl-4-hydroxyphenyl)-1H-indazol-3-yl)-5-isopropyl-4,5,6,7-tetrahydro-3H-imidazo[4,5-c]pyridine-6-carboxylic acid (40 mg, 0.090 mmol) (I-19) N,N,3-trimethylazetidin-3-amine hydrochloride (20.29 mg, 0.135 mmol), and DIPEA (0.047 mL, 0.269 mmol) were dissolved in DMF (1.50 mL), then HATU (51.2 mg, 0.135 mmol) was added and the reaction mixture was stirred at room temperature for 16 hours (reaction progress was monitored by LCMS). Hydrazine (8.45 µl, 0.269 mmol) was added to cleave undesired byproducts, then the solution was stirred at room temperature for 10 minutes. The reaction mixture was then concentrated and the crude product was purified by preparative HPLC (5-60% ACN/Water gradient, C18 column) to provide the TFA salt of the title compound (26 mg, 38% yield). (m/z): [M+H]+ calcd for $C_{31}H_{39}N_7O_2$ 542.32 found 542.2.

Example 12: (S)-(3-(dimethylamino)azetidin-1-yl) (2-(6-(2-ethyl-4-hydroxyphenyl)-1H-indazol-3-yl)-5-propyl-4,5,6,7-tetrahydro-3H-imidazo[4,5-c]pyridin-6-yl)methan One

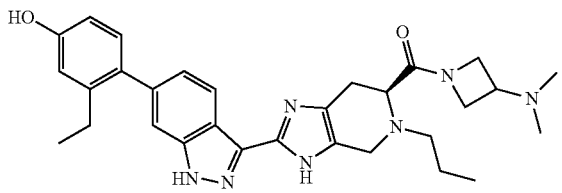

(S)-2-(6-(2-ethyl-4-hydroxyphenyl)-1H-indazol-3-yl)-5-propyl-4,5,6,7-tetrahydro-3H-imidazo[4,5-c]pyridine-6-carboxylic acid, TFA (30 mg, 0.054 mmol), (I-20) 3-(dimethylamino)azetidine dihydrochloride (13.92 mg, 0.080 mmol), and DIPEA (0.047 mL, 0.268 mmol) were dissolved in DMF (1.50 mL), then HATU (30.6 mg, 0.080 mmol) was added and the reaction mixture was stirred at room temperature for 1 hour (reaction progress was monitored by LCMS). Hydrazine (5.05 µl, 0.161 mmol) was added to cleave undesired byproducts, then the solution was stirred at room temperature for 10 minutes. The reaction mixture was then concentrated and the crude product was purified by preparative HPLC (5-60% ACN/Water gradient, C18 column) to provide the TFA salt of the title compound (26 mg, 63% yield). (m/z): [M+H]+ calcd for $C_{30}H_{37}N_7O_2$ 528.30 found 528.2.

Example 13: (S)-(3-(dimethylamino)-3-methylazetidin-1-yl)(2-(6-(2-ethyl-4-hydroxyphenyl)-1H-indazol-3-yl)-5-propyl-4,5,6,7-tetrahydro-3H-imidazo[4,5-c]pyridin-6-yl)methan One

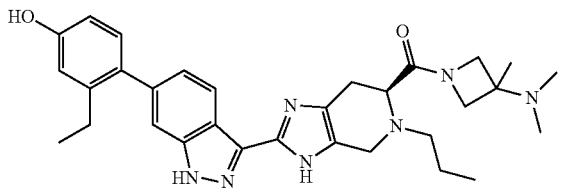

(S)-2-(6-(2-ethyl-4-hydroxyphenyl)-1H-indazol-3-yl)-5-propyl-4,5,6,7-tetrahydro-3H-imidazo[4,5-c]pyridine-6-carboxylic acid, TFA (30 mg, 0.054 mmol), (I-20) N,N,3-Trimethylazetidin-3-amine hydrochloride (12.12 mg, 0.080 mmol), and DIPEA (0.047 mL, 0.268 mmol) were dissolved in DMF (1.50 mL), then HATU (30.6 mg, 0.080 mmol) was added and the reaction mixture was stirred at room temperature for 1 hour (reaction progress was monitored by LCMS). Hydrazine (5.05 µl, 0.161 mmol) was added to cleave undesired byproducts, then the solution was stirred at room temperature for 10 minutes. The reaction mixture was then concentrated and the crude product was purified by preparative HPLC (5-60% ACN/Water gradient, C18 column) to provide the TFA salt of the title compound (18 mg, 44% yield). (m/z): [M+H]+ calcd for $C_{31}H_{39}N_7O_2$ 542.32 found 542.2.

Biological Assays

The compounds of the disclosure have been characterized in one or more of the following biological assays.

Assay 1: Biochemical JAK Kinase Assays

A panel of four LanthaScreen JAK biochemical assays (JAK1, 2, 3 and Tyk2) were carried in a common kinase reaction buffer (50 mM HEPES, pH 7.5, 0.01% Brij-35, 10 mM $MgCl_2$, and 1 mM EGTA). Recombinant GST-tagged JAK enzymes and a GFP-tagged STAT1 peptide substrate were obtained from Life Technologies.

Serially diluted compounds were pre-incubated with each of the four JAK enzymes and the substrate in white 384-well microplates (Corning) at ambient temperature for 1 h. ATP was subsequently added to initiate the kinase reactions in 10 µL total volume, with 1% DMSO. The final enzyme concentrations for JAK1, 2, 3 and Tyk2 are 4.2 nM, 0.1 nM, 1 nM, and 0.25 nM respectively; the corresponding Km ATP concentrations used are 25 µM, 3 µM, 1.6 µM, and 10 µM; while the substrate concentration is 200 nM for all four assays. Kinase reactions were allowed to proceed for 1 hour at ambient temperature before a 10 µL preparation of EDTA (10 mM final concentration) and Tb-anti-pSTAT1 (pTyr701) antibody (Life Technologies, 2 nM final concentration) in TR-FRET dilution buffer (Life Technologies) was added. The plates were allowed to incubate at ambient temperature for 1 h before being read on the EnVision reader (Perkin Elmer). Emission ratio signals (520 nm/495 nm) were recorded and utilized to calculate the percent inhibition values based on DMSO and background controls.

For dose-response analysis, percent inhibition data were plotted vs. compound concentrations, and $IC_{50}$ values were determined from a 4-parameter robust fit model with the Prism software (GraphPad Software). Results were expressed as $pIC_{50}$ (negative logarithm of $IC_{50}$) and subsequently converted to pKi (negative logarithm of dissociation constant, Ki) using the Cheng-Prusoff equation.

Test compounds having a lower Ki value or higher pKi value in each of the four JAK assays show greater inhibition of JAK activity.

Assay 2: Inhibition of IL-2 Stimulated pSTAT5 in Tall-1 T Cells

The potency of test compounds for inhibition of interleukin-2 (IL-2) stimulated STAT5 phosphorylation was measured in the Tall-1 human T cell line (DSMZ) using AlphaLisa. Because IL-2 signals through JAK1/3, this assay provides a measure of JAK1/3 cellular potency.

Phosphorylated STAT5 was measured via the AlphaLISA SureFire Ultra pSTAT5 (Tyr694/699) kit (PerkinElmer).

Human T cells from the Tall-1 cell line were cultured in a 37° C., 5% $CO_2$ humidified incubator in RPMI (Life Technologies) supplemented with 15% Heat Inactivated Fetal Bovine Serum (FBS, Life Technologies), 2 mM Glutamax (Life Technologies), 25 mM HEPES (Life Technologies) and 1×Pen/Strep (Life Technologies). Compounds were serially diluted in DMSO and dispensed acoustically to empty wells. Assay media (phenol red-free DMEM (Life Technologies) supplemented with 10% FBS (ATCC)) was dispensed (4 µL/well) and plates shaken at 900 rpm for 10 mins. Cells were seeded at 45,000 cells/well in assay media (4 µL/well), and incubated at 37° C., 5% $CO_2$ for 1 hour, followed by the addition of IL-2 (R&D Systems; final concentration 300 ng/mL) in pre-warmed assay media (4 µL) for 30 minutes. After cytokine stimulation, cells were lysed with 6 ul of 3× AlphaLisa Lysis Buffer (PerkinElmer) containing 1× PhosStop and Complete tablets (Roche). The lysate was shaken at 900 rpm for 10 minutes at room temperature (RT). Phosphorylated STAT5 was measured via the pSTAT5 AlphaLisa kit (PerkinElmer). Freshly prepared acceptor bead mixture was dispensed onto lysate (5 μL) under green filtered <100 lux light. Plates were shaken at 900 rpm for 2 mins, briefly spun down, and incubated for 2 hrs at RT in the dark. Donor beads were dispensed (5 μL) under green filtered <100 lux light. Plates were shaken at 900 rpm for 2 minutes, briefly spun down, and incubated overnight at RT in the dark. Luminescence was measured with excitation at 689 nm and emission at 570 nm using an EnVision plate reader (PerkinElmer) under green filtered <100 lux light.

To determine the inhibitory potency of test compounds in response to IL-2, the average emission intensity of beads bound to pSTAT5 was measured in a human T cell line. $IC_{50}$ values were determined from analysis of the inhibition curves of signal intensity versus compound concentration. Data are expressed as $pIC_{50}$ (negative decadic logarithm $IC_{50}$) values (mean±standard deviation).

In Vitro Assay Results

The compounds of the disclosure were tested in the four JAK enzyme assays; JAK1, JAK2, JAK3, and Tyk2, and the BEAS-2B cellular potency assay described above.

TABLE 1

| Example Number | JAK1 $pK_i$ | JAK2 $pK_i$ | JAK3 $pK_i$ | Tyk2 $pK_i$ | Tall-1 pIC50 |
|---|---|---|---|---|---|
| 1 | 10.2 | 10.3 | 9.8 | 9.0 | 8.8 |
| 2 | 10.3 | 10.2 | 9.8 | 8.9 | 8.4 |
| 3 | 10.2 | 10.4 | 10.2 | 9.3 | 8.8 |
| 4 | 10.1 | 10.4 | 10.1 | 9.0 | 8.6 |
| 5 | 10.3 | 10.5 | 10.1 | 9.2 | 8.8 |
| 6 | 10.2 | 10.4 | 10.0 | 9.0 | 8.7 |
| 7 | 10.2 | 10.5 | 10.2 | 9.1 | 8.6 |
| 8 | 10.4 | 10.8 | 10.1 | 9.5 | 8.8 |
| 9 | 10.3 | 10.7 | 10.3 | 9.2 | 8.7 |
| 10 | 10.4 | 10.6 | 10.2 | 9.1 | 8.6 |
| 11 | 10.0 | 10.8 | 9.9 | 9.1 | 8.7 |
| 12 | 10.5 | 10.6 | 10.3 | 9.0 | 8.7 |
| 13 | 10.3 | 10.5 | 9.8 | 9.0 | 8.6 |

Assay 3: Murine (Mouse) Model of IL-13 Induced pSTAT6 Induction in Lung Tissue

IL-13 is an important cytokine underlying the pathophysiology of asthma (Kudlacz et al. *Eur. J. Pharmacol*, 2008, 582, 154-161). IL-13 binds to cell surface receptors activating members of the Janus family of kinases (JAK) which then phosphorylate STAT6 and subsequently activates further transcription pathways. In the described model, a dose of IL-13 was delivered locally into the lungs of mice to induce the phosphorylation of STAT6 (pSTAT6) which is then measured as the endpoint.

Adult Balb/c mice from Harlan were used in the assay. On the day of study, animals were lightly anesthetized with isoflurane and administered either vehicle or test compound (1 mg/mL, 50 μL total volume over several breaths) via oral aspiration. Animals were placed in lateral recumbency post dose and monitored for full recovery from anesthesia before being returned to their home cage. Four hours later, animals were once again briefly anesthetized and challenged with either vehicle or IL-13 (0.03 μg total dose delivered, 50 μL total volume) via oral aspiration before being monitored for recovery from anesthesia and returned to their home cage. One hour after vehicle or IL-13 administration, whole blood and lungs were collected for both pSTAT6 detection in lung homogenates using a Perkin Elmer AlphaLISA® SureFire® Ultra™ HVp-STAT6 (Tyr641) assay kit and for total drug concentration analysis in both lung and plasma. Blood samples were centrifuged (Eppendorf centrifuge, 5804R) for 4 minutes at approximately 12,000 rpm at 4° C. to collect plasma. Lungs were rinsed in DPBS (Dulbecco's Phosphate-Buffered Saline), padded dry, flash frozen, weighed, and homogenized at a dilution of 1:3 in 0.1% formic acid in HPLC water. Plasma and lung levels of test compound were determined by LC-MS analysis against analytical standards constructed into a standard curve in the test matrix. A lung to plasma ratio was determined as the ratio of the lung concentration in ng/g to the plasma concentration in ng/mL at 5 hours.

Activity in the model is evidenced by a decrease in the level of pSTAT6 present in the lungs of treated animals at 5 hours compared to the vehicle treated, IL-13 challenged control animals. The difference between the control animals which were vehicle-treated, IL-13 challenged and the control animals which were vehicle-treated, vehicle challenged dictated the 0% and 100% inhibitory effect, respectively, in any given experiment. The compounds tested in the assay exhibited inhibition of STAT6 phosphorylation at 5 hours after IL-13 challenge as documented below.

TABLE 2 pSTAT6 Inhibition and Plasma/Lung Exposure Observed

| Compound | Lung Concentration (ng/g) at 5 hr | Plasma Concentration (ng/mL) at 5 hr | Lung to Plasma ratio at 5 hr | pSTAT6 inhibition at 5 hours |
|---|---|---|---|---|
| 1 | 13000 ± 5720 | 10.3 ± 3.9 | 1262 | 67 |
| 2 | 23450 ± 12528 | 17.5 ± 25 | 1340 | 72 |
| 3 | 6330 ± 1131 | 15.4 ± 7 | 411 | 76 |
| 4 | 17350 ± 6625 | 22.0 ± 23 | 788 | 67 |
| 5 | 5445 ± 1862 | 13.0 ± 3.7 | 418 | 73 |
| 6 | 11600 ± 4682 | 11.3 ± 5.7 | 1026 | 37 |
| 7 | 10155 ± 1979 | 24.0 ± 16.2 | 423 | 75 |
| 8 | 22138 ± 5547 | 58 ± 17 | 381 | 51 |
| 9 | 7750 ± 1652 | 23 ± 6 | 339 | 72 |
| 10 | 5130 ± 2205 | 24 ± 6 | 216 | 73 |
| 11 | 15000 ± 3349 | 55 ± 21 | 271 | 72 |
| 12 | 6940 ± 4248 | 25 ± 9 | 281 | 55 |
| 13 | 7465 ± 3084 | 23 ± 2.5 | 330 | 66 |

Observation of significant concentration in compounds tested in the mouse lung confirmed that the observed inhibition of IL-13 induced pSTAT6 induction was a result of the activity of the test compound. The lung to plasma ratio at 5 hours showed that compounds 1 to 6 exhibited significantly more exposure in the lung than exposure in plasma in mice.

Assay 4: Inhibition of TSLP-Evoked TARC Release in Human Peripheral Blood Mononuclear Cells Thymic stromal lymphopoietin (TSLP) and thymus and activation-regulated chemokine (TARC) are overexpressed in asthmatic airways, and correlate with disease severity. In the lungs, TSLP may be released by bronchial epithelial cells in response to allergens and viral infections. TSLP signals through an IL-7Rα/TSLPR heterodimer found in a broad range of tissues and cell types, including epithelial cells, endothelial cells, neutrophils, macrophages, and mast cells. The binding of TSLP to its receptor induces a conformational change that activates JAK1 and JAK2 to phosphorylate various transcription factors, including STAT3 and STAT5. In immune cells, this triggers a cascade of intracellular events that result in cell proliferation, anti-apoptosis, dendritic cell migration, and production of Th2 cytokines and chemokines. In peripheral blood mononuclear cells (PBMC), TSLP has a proinflammatory effect by activating myeloid dendritic cells to attract and stimulate T cells, a process mediated by the chemoattractant TARC.

In this assay, it was shown that TSLP stimulation induces TARC release from PBMCs, and that this response is attenuated in a dose-dependent manner upon treatment with compound. The potencies of the test compounds were measured for inhibition of TARC release.

PBMC aliquots (previously isolated from whole blood and frozen in aliquots at −80° C.) from 3 to 5 donors were thawed at 37° C. and added dropwise to 40 mL pre-warmed, sterile-filtered, complete RPMI media in 50 mL Falcon tubes. Cells were pelleted and resuspended in complete media at $2.24 \times 10^6$ cells/mL. Cells were seeded at 85 µL (190,000 cells) per well in a tissue culture treated 96-well flat bottom microplate. Cells were allowed to rest for 1 hour at 37° C. with 5% $CO_2$.

Compounds were received as 10 mM stock solutions in DMSO. 3.7-fold serial dilutions were performed to generate 9 concentrations of test compound in DMSO at 300× the final assay test concentration. 150-fold intermediate dilutions were performed in complete media to generate compound at 2× the final assay test concentration with 0.2% DMSO. After the 1 hour rest period, 95 µL of 2× compound was added to each well of PBMC, for a final assay concentration range of 33.33 µM to 0.95 µM. 95 µL of 0.2% DMSO in complete media was added to the untreated control wells. Cells were pre-treated with compound for 1 hour at 37° C. with 5% $CO_2$ prior to stimulation.

Recombinant human TSLP protein was reconstituted at 10 ug/mL in sterile DPBS with 0.1% BSA and stored in aliquots at −20° C. Immediately prior to use, an aliquot was thawed and prepared at 20× the final assay concentration in complete media. 10 µL of 20×TSLP was added to each well of PBMC, for a final assay concentration of 10 ng/mL. 10 µL of complete media was added to the unstimulated control wells. Cells were stimulated in the presence of compound for 48 hours at 37° C. with 5% $CO_2$.

Following stimulation, the cell culture supernatants were harvested and TARC levels were detected by enzyme-linked immunosorbent assay (ELISA), using Human CCL17/TARC Quantikine ELISA Kit (R&D Systems # DDN00) according to the manufacturer's instructions.

For dose response analysis, the log [test compound (M)] was plotted versus the percent response values for each donor, and $IC_{50}$ values were determined using a nonlinear regression analysis with GraphPad Prism Software using the 4-parameter sigmoidal dose-response algorithm with variable slope. Data are expressed as mean $pIC_{50}$ (negative decadic logarithm $IC_{50}$) values calculated from $pIC_{50}$ values of individual donors and rounded to one decimal place. The potency values for inhibition are summarized in Table 3.

TABLE 3

Potency ($pIC_{50}$) Values of Test Compounds for Inhibition of TSLP-evoked TARC Release in Human Peripheral Blood Mononuclear Cells

| Compound | pIC50 ± st. dev. |
|---|---|
| 1 | 7.1 ± 0.1 |
| 2 | 6.8 ± 0.2 |
| 3 | 7.3 ± 0.2 |
| 4 | 6.8 ± 0.1 |
| 5 | 7.5 ± 0.6 |
| 6 | 6.8 ± 0.2 |
| 7 | 7.2 ± 0.1 |
| 8 | 7.0 ± 0.1 |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. Additionally, all publications, patents, and patent documents cited hereinabove are incorporated by reference herein in full, as though individually incorporated by reference.

What is claimed is:

1. A process for preparing a compound of formula J-15, or a salt thereof:

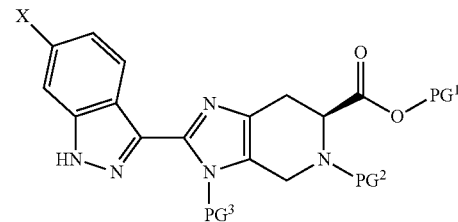

J-15 wherein
X is selected from the group consisting of Br, I and Cl;
$PG^1$ is a carboxylic acid protecting group;
$PG^2$ is an amino protecting group; and
$PG^3$ is an amino protecting group;
the process comprising:
 (a) reacting a compound of Formula J-14:

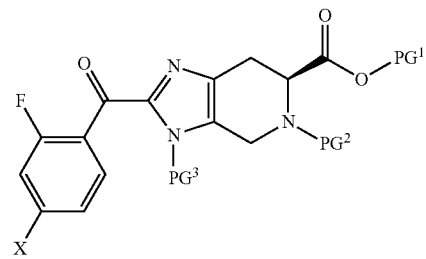

J-14 or a salt thereof, with hydrazine to give the compound of formula J-15 and
 (b) optionally forming a salt of compound J-15.

2. The process of claim 1, wherein the reaction with hydrazine is conducted at 60° C.±20° C.

3. The process of claim 1,
wherein
X is selected from the group consisting of Br, I and Cl;
$PG^1$ is an alkyl or benzyl group wherein the benzyl group is optionally substituted;
$PG^2$ is selected from the group consisting of an acyl group, an alkoxycarbonyl group, an arylmethyl group, and a silyl group; and
$PG^3$ is selected from the group consisting of an acyl group, an alkoxycarbonyl group, an arylmethyl group, and a silyl group.

4. The process of claim 1, wherein X is Br, $PG^1$ is benzyl, $PG^2$ is tert-butoxycarbonyl and $PG^3$ is benzyl.

5. The process of claim 1, wherein compound J-14, or a salt thereof, is prepared by:

(a) reacting a compound of formula J-13:

[Structure J-13: 2-fluoro-4-X-benzoyl-Y]

wherein Y is a leaving group, with a compound of formula J-11:

[Structure J-11: imidazo-tetrahydropyridine with CO-O-PG¹, N-PG², N-PG³]

in the presence of a base, to give J-14, and (b) optionally forming a salt of compound J-14.

6. The process of claim 5, wherein Y is Cl.

7. A compound of formula J-14:

[Structure J-14]

or a salt thereof, wherein

X is selected from the group consisting of Br, I and Cl;

PG¹ is a carboxylic acid protecting group;

PG² is an amino protecting group; and

PG³ is an amino protecting group.

8. The compound of claim 7, or a salt thereof, wherein

X is selected from the group consisting of Br, I and Cl;

PG¹ is an alkyl or benzyl group wherein the benzyl group is optionally substituted;

PG² is selected from the group consisting of an acyl group, an alkoxycarbonyl group, an arylmethyl group, and a silyl group; and PG³ is selected from the group consisting of an acyl group, an alkoxycarbonyl group, an arylmethyl group, and a silyl group.

9. The compound of claim 7, having the formula I-14:

[Structure I-14]

or a salt thereof.

10. A compound of formula J-15:

[Structure J-15]

or a salt thereof, wherein

X is selected from the group consisting of Br, I and Cl;

PG¹ is a carboxylic acid protecting group;

PG² is an amino protecting group; and

PG³ is an amino protecting group.

11. The compound of claim 10, or a salt thereof, wherein

X is selected from the group consisting of Br, I and Cl;

PG¹ is an alkyl or benzyl group wherein the benzyl group is optionally substituted;

PG² is selected from the group consisting of an acyl group, an alkoxycarbonyl group, an arylmethyl group, and a silyl group; and PG³ is selected from the group consisting of an acyl group, an alkoxycarbonyl group, an arylmethyl group, and a silyl group.

12. The compound of claim 10 having the formula I-15:

[Structure I-15]

or a salt thereof.

13. A process for preparing a compound of formula J-16, or a salt thereof:

J-16

[Structure of J-16: biaryl compound with PG⁴-O, R substituent, ethyl group, indazole (HN-N), imidazole-fused tetrahydropyridine with PG³ on N, PG² on N, and carboxylate -C(O)-O-PG¹]

wherein
PG¹ is a carboxylic acid protecting group;
PG² is an amino protecting group;
PG³ is an amino protecting group;
PG⁴ is an hydroxyl protecting group; and
R is H or F;
the process comprising:
(a) reacting a compound of formula J-13:

J-13

[Structure of J-13: 2-fluoro-4-X-benzoyl-Y]

wherein X is selected from the group consisting of Br, I and Cl; and Y is a leaving group;
with a compound of formula J-11:

J-11

[Structure of J-11: imidazole-fused tetrahydropyridine with PG³, PG², and -C(O)-O-PG¹]

in the presence of a base, to give a compound of formula J-14:

J-14

[Structure of J-14: acylated product with 2-fluoro-4-X-benzoyl group attached to imidazole]

and optionally forming a salt of compound J-14;
(b) reacting the compound of formula J-14, or a salt thereof, with hydrazine to give a compound of formula J-15:

J-15

[Structure of J-15: X-substituted indazole linked to imidazole-fused tetrahydropyridine with PG¹, PG², PG³]

and optionally forming a salt of compound J-15;
(c) reacting the compound of Formula J-15, or a salt thereof, with a compound of formula J-5, J-6 or J-7:

J-5

[Structure: PG⁴-O-aryl with R, ethyl, BF₃K]

J-6

[Structure: PG⁴-O-aryl with R, ethyl, B(OH)₂]

J-7

[Structure: PG⁴-O-aryl with R, ethyl, B(ORᵃ)(ORᵇ)]

wherein $R^a$ and $R^b$ are each independently selected from $C_{1-8}$ alkyl, wherein $R^a$ and $R^b$ may optionally be joined to form a 4 to 8 membered ring; in the presence of a base, a palladium catalyst and a phosphine ligand to give the compound of formula J-16, and optionally forming a salt of compound J-16.

14. The process of claim 13, wherein step (c) is conducted in the presence of a diboron reagent or a catalyst.

15. The process of claim 14, wherein step (c) is conducted in the presence of tetrahydroxydiboron, a diboronic ester or the product of the reaction of bis(pinacolato)diboron with potassium fluoride hydrofluoride.

16. The process of claim 13, wherein the reaction with hydrazine in step (b) is conducted at 60° C.±20° C.

17. The process of claim 13, wherein

X is selected from the group consisting of Br, I and Cl;

$PG^1$ is an alkyl or benzyl group wherein the benzyl group is optionally substituted;

$PG^2$ is selected from the group consisting of an acyl group, an alkoxycarbonyl group, an arylmethyl group, and a silyl group;

$PG^3$ is selected from the group consisting of an acyl group, an alkoxycarbonyl group, an arylmethyl group, and a silyl group;

$PG^4$ is selected from the group consisting of a silyl group, an acyl group, and an arylmethyl group.

18. The process of claim 13, wherein X is Br, $PG^1$ is benzyl, $PG^2$ is tert-butoxycarbonyl $PG^3$ is benzyl, and $PG^4$ is benzyl.

19. The process of claim 13, wherein Y is Cl.

20. The process of claim 13, wherein the palladium catalyst and phosphine ligand of step (c) are bis(di-tert-butyl (4-dimethylaminophenyl)phosphine)dichloropalladium(II).

21. The process of claim 13, wherein a compound of formula J-5 is used in step (c).

\* \* \* \* \*